US008440449B2

(12) United States Patent
Hughes et al.

(10) Patent No.: US 8,440,449 B2
(45) Date of Patent: May 14, 2013

(54) **TRANSFORMED *SACCHAROMYCES CEREVISIAE* ENGINEERED FOR XYLOSE UTILIZATION**

(75) Inventors: Stephen R. Hughes, Peoria, IL (US); Tauseef R. Butt, Malvern, PA (US)

(73) Assignees: The United States of America, as represented by the Secretary of Agriculture, Washington, DC (US); LifeSensors, Inc., Malvern, PA (US)

( * ) Notice: Subject to any disclaimer, the term of this patent is extended or adjusted under 35 U.S.C. 154(b) by 519 days.

(21) Appl. No.: 12/568,071

(22) Filed: Sep. 28, 2009

(65) Prior Publication Data

US 2010/0112658 A1 May 6, 2010

Related U.S. Application Data

(60) Provisional application No. 61/101,399, filed on Sep. 30, 2008.

(51) Int. Cl.
*C12N 1/00* (2006.01)
*C07H 21/04* (2006.01)

(52) U.S. Cl.
USPC ...................................... 435/252.1; 536/23.1

(58) Field of Classification Search ........................ None
See application file for complete search history.

(56) References Cited

U.S. PATENT DOCUMENTS 7,083,941 B2 8/2006 Butt et al.
7,226,735 B2 6/2007 Jeffries et al.
7,910,364 B2 * 3/2011 Lima et al. ................. 435/320.1
2006/0216804 A1 9/2006 Karhumaa
2007/0082386 A1 4/2007 Gorwa-Grauslund
2007/0184546 A1 8/2007 Farrelly et al.
2008/0014620 A1 1/2008 Camp et al.
2010/0028975 A1 2/2010 Gorwa-Grauslund

FOREIGN PATENT DOCUMENTS

WO 2005/091733 A2 10/2005

OTHER PUBLICATIONS

Kuyper et al., "Metabolic engineering of a xylose-isomerase-expressing *Saccharomyces cerevisiae* strain for rapid anaerobic xylose fermentation", FEMS Yeast Research 5: 399-409 (2005).*

Parkhill et al.,"Genome sequence of *Yersinia pestis*, the causative agent of plague", Nature 413: 523-527 (Oct. 4, 2001).*

Lonn, A., et al., Xylose isomerase activity influences xylose fermentation with recombinant *Saccharomyces cerevisiae* strains expressing mutated xyIA from *Thermus thermophilus* (2003).

Karhumaa, Kaisa, et al., Comparison of the xylose reductase-xylitol dehydrogenase and the xylose isomerase pathways for xylose fermentation by recombinant *Saccharomyces cerev* (2007).

* cited by examiner

*Primary Examiner* — Anand Desai
(74) *Attorney, Agent, or Firm* — John Fado; Randall E. Deck; Lesley Shaw

(57) ABSTRACT

Recombinant *Saccharomyces cerevisiae* produced by transformation with heterologous polynucleotide sequences coding for xylulokinase (XKS) from *Yersinia pestis* and xylose isomerase (XI) are capable of xylose utilization. The transformants express these heterologous polynucleotides at a sufficient functional level to grow aerobically on xylose as the sole carbon source. Further transformation of the recombinant yeasts to overexpress one or more of the *S cerevisiae* genes PIP2, IMG2, MAK5, VPS9, COX10, ALE1, CDC7, and MMS4, permits the yeast to grow anaerobically on xylose as the sole carbon source. When grown under anaerobic conditions on a culture medium comprising both glucose and xylose, the transformed yeast exhibit increased ethanol productivity, with the yeast growing on the xylose to increase their biomass and fermenting the glucose to ethanol.

20 Claims, 6 Drawing Sheets

A.

B.

D.

SEQUENCE LISTING

```
<160> NUMBER OF SEQ ID NOS: 31

<210> SEQ ID NO 1
<211> LENGTH: 31
<212> TYPE: PRT
<213> ORGANISM: Saccharomyces cerevisiae

<400> SEQUENCE: 1

Met Gly His His His His His His Gly Thr Ser Leu Tyr Lys Lys Ala
1               5                   10                  15

Gly Ser Ala Ala Ala Pro Phe Thr Met His His His His His His
            20                  25                  30


<210> SEQ ID NO 2
<211> LENGTH: 22
<212> TYPE: PRT
<213> ORGANISM: Saccharomyces cerevisiae

<400> SEQUENCE: 2

Thr Ser Leu Tyr Lys Lys Ala Gly Ser Ala Ala Ala Pro Phe Thr Met
1               5                   10                  15

His His His His His His
            20


<210> SEQ ID NO 3
<211> LENGTH: 35
<212> TYPE: DNA
<213> ORGANISM: Saccharomyces cerevisiae

<400> SEQUENCE: 3

cgcgagctag ccgcgcgttt cggtgatgac ggtga                                35


<210> SEQ ID NO 4
<211> LENGTH: 35
<212> TYPE: DNA
<213> ORGANISM: Saccharomyces cerevisiae

<400> SEQUENCE: 4

cgcgacgcgt gatcggcaag tgcacaaaca atact                                35


<210> SEQ ID NO 5
<211> LENGTH: 35
<212> TYPE: DNA
<213> ORGANISM: Saccharomyces cerevisiae

<400> SEQUENCE: 5

cgcgacgcgt ttaagcaagg attttcttaa cttct                                35


<210> SEQ ID NO 6
<211> LENGTH: 37
<212> TYPE: DNA
```

<213> ORGANISM: Saccharomyces cerevisiae

<400> SEQUENCE: 6
cgcgagctag ccgactggaa agcgggcagt gagcgca 37

<210> SEQ ID NO 7
<211> LENGTH: 30
<212> TYPE: DNA
<213> ORGANISM: Piromyces sp.

<400> SEQUENCE: 7
caccatgcat catcatcatc atcatatggc 30

<210> SEQ ID NO 8
<211> LENGTH: 106
<212> TYPE: DNA
<213> ORGANISM: Piromyces sp.

<400> SEQUENCE: 8
caccatgcat catcatcatc atcatatggc taaggaatat ttcccacaaa ttcaaaagat 60
taagttcgaa ggtaaggatt ctaagaatcc attagccttc cactac 106

<210> SEQ ID NO 9
<211> LENGTH: 110
<212> TYPE: DNA
<213> ORGANISM: Piromyces sp.

<400> SEQUENCE: 9
ttaaccttcg gcgcaaagag tgtgccacca ggccatggcg aaacgtaacc aatccttcat 60
tttcttaccc atgacttcct tttcagcatc gtagtagtgg aaggctaatg 110

<210> SEQ ID NO 10
<211> LENGTH: 110
<212> TYPE: DNA
<213> ORGANISM: Piromyces sp.

<400> SEQUENCE: 10
caacatcgtg gaaacagtag tatggaatac caagcttttg catgatttcg aaaccagcat 60
caaccttttg cttggcaatt tcaatagcat cagtaccttc gttccatggg 110

<210> SEQ ID NO 11
<211> LENGTH: 110
<212> TYPE: DNA
<213> ORGANISM: Piromyces sp.

<400> SEQUENCE: 11
aagatcaaca tcgtggaaac agtagtatgg aataccaagc ttttgcatga tttcgaaacc 60
agcatcaacc ttttgcttgg caatttcaat agcatcagta ccttcgttcc 110

<210> SEQ ID NO 12
<211> LENGTH: 110
<212> TYPE: DNA
<213> ORGANISM: Piromyces sp.

<400> SEQUENCE: 12
tccttttgct tttccttgag gtaagcaacg acagccttaa ggttggattc gtattcttca 60
atagagttac cttcggaaac aagatcaaca tcgtggaaac agtagtatgg 110

<210> SEQ ID NO 13
<211> LENGTH: 110
<212> TYPE: DNA

<213> ORGANISM: Piromyces sp.

<400> SEQUENCE: 13
ctgggttagt ggaggcaccg ttcatgtaac gcttgtgacc gaagacgtta gcagtactcc 60
agagaagctt aataccggtt tccttttgct tttccttgag gtaagcaacg 110

<210> SEQ ID NO 14
<211> LENGTH: 109
<212> TYPE: DNA
<213> ORGANISM: Piromyces sp.

<400> SEQUENCE: 14
gttttcagca ccaagttcaa taccggcgtc tatggcgttc ttaatttgaa caatagcacg 60
ggcgacaaca tcaaagtctg ggttagtgga ggcaccgttc atgtaacgc 109

<210> SEQ ID NO 15
<211> LENGTH: 110
<212> TYPE: DNA
<213> ORGANISM: Piromyces sp.

<400> SEQUENCE: 15
atagtggcca tgtgttcctt ttcacgcttt tggtcagtgt taaggagact catgtaacct 60
tcacgaccac cccagaagac gtagttttca gcaccaagtt caataccggc 110

<210> SEQ ID NO 16
<211> LENGTH: 110
<212> TYPE: DNA
<213> ORGANISM: Piromyces sp.

<400> SEQUENCE: 16
tggttggttc cattggcttt ggttcaatga ggaaagtacc cttgaatccc ttggaacgag 60
cgtagtcacg agccatggta agcatagtgg ccatgtgttc cttttcacgc 110

<210> SEQ ID NO 17
<211> LENGTH: 110
<212> TYPE: DNA
<213> ORGANISM: Piromyces sp.

<400> SEQUENCE: 17
tgaccttgaa gtccttgtct aagttgtggg ccttaaggaa accaatagcg gtttcagtgt 60
caacatcgta ttggtgcttg gttggttcca ttggctttgg ttcaatgagg 110

<210> SEQ ID NO 18
<211> LENGTH: 110
<212> TYPE: DNA
<213> ORGANISM: Piromyces sp.

<400> SEQUENCE: 18
gcataccagc atcaacagca caggcaagtt cgtgttcgaa agtgtgacca gcaagagtag 60
cgtggttaac ttcaatgttg accttgaagt ccttgtctaa gttgtgggcc 110

<210> SEQ ID NO 19
<211> LENGTH: 110
<212> TYPE: DNA
<213> ORGANISM: Piromyces sp.

<400> SEQUENCE: 19
gttcgtattg atcaattggg aattgatcag tatcccaacc gttttggtag tcaccacggt 60
tagcatcaat ggaaccgagc ataccagcat caacagcaca ggcaagttcg 110

<210> SEQ ID NO 20
<211> LENGTH: 110
<212> TYPE: DNA
<213> ORGANISM: Piromyces sp.

<400> SEQUENCE: 20
acgacgagtc ttggcatcga agttggtacc accagtaacg aaaccaccac cacggatgat 60
ttccatccaa gcttggacga gttcgtattg atcaattggg aattgatcag 110

<210> SEQ ID NO 21
<211> LENGTH: 110
<212> TYPE: DNA
<213> ORGANISM: Piromyces sp.

<400> SEQUENCE: 21
cttggcagcg ttttcaagag cacgagccat agcatccata ccagaaacgt gggcaatgat 60
gatgtcttcg aggtcagtag agttacgacg agtcttggca tcgaagttgg 110

<210> SEQ ID NO 22
<211> LENGTH: 110
<212> TYPE: DNA
<213> ORGANISM: Piromyces sp.

<400> SEQUENCE: 22
aagtccttac caataccact gtcgaaggaa gcgtaacgtt ccttcttcat cttggtgtat 60
ggagattctt ggaggagctt ggcagcgttt tcaagagcac gagccatagc 110

<210> SEQ ID NO 23
<211> LENGTH: 110
<212> TYPE: DNA
<213> ORGANISM: Piromyces sp.

<400> SEQUENCE: 23
taccagaagt ttgctttggt tcaccgttct tcttaccgta ttcgtaaact tgttcgaggg 60
tgagcttacc atcttcaaag tccttaccaa taccactgtc gaaggaagcg 110

<210> SEQ ID NO 24
<211> LENGTH: 94
<212> TYPE: DNA
<213> ORGANISM: Piromyces sp.

<400> SEQUENCE: 24
ttaactacga ttaacttatt ggtacatggc aacaatagct tcgtagagtt cttgcttacc 60
agaagtttgc tttggttcac cgttcttctt accg 94

<210> SEQ ID NO 25
<211> LENGTH: 25
<212> TYPE: DNA
<213> ORGANISM: Piromyces sp.

<400> SEQUENCE: 25
ttaactacga ttaacttatt ggtac 25

<210> SEQ ID NO 26
<211> LENGTH: 70
<212> TYPE: DNA
<213> ORGANISM: Saccharomyces cerevisiae

<400> SEQUENCE: 26
catttcagca atatatatat atatatttca aggatatacc attctaatgt ctgttattaa 60

-continued

```
tttcacaggt                                                              70


<210> SEQ ID NO 27
<211> LENGTH: 69
<212> TYPE: DNA
<213> ORGANISM: Saccharomyces cerevisiae

<400> SEQUENCE: 27

tttcatttat aaagtttatg tacaaatatc ataaaaaaag agaatctttc tatttcttag      60

catttttga                                                               69


<210> SEQ ID NO 28
<211> LENGTH: 22
<212> TYPE: DNA
<213> ORGANISM: Piromyces sp.

<400> SEQUENCE: 28

atggctaagg aatatttccc ac                                                22


<210> SEQ ID NO 29
<211> LENGTH: 28
<212> TYPE: DNA
<213> ORGANISM: Piromyces sp.

<400> SEQUENCE: 29

cgaagctatt gttgccatgt accaataa                                          28


<210> SEQ ID NO 30
<211> LENGTH: 88
<212> TYPE: DNA
<213> ORGANISM: Artificial
<220> FEATURE:
<223> OTHER INFORMATION: Synthetic sequence from bacteria Yersinia
      pestis with a RGS tetra HIS tag

<400> SEQUENCE: 30

caccatgaga ggttctcatc accatcaccc aactttgtac aaaaaagcag gctccgcggc      60

cgcccccttc accatgtatg ttggtatc                                          88


<210> SEQ ID NO 31
<211> LENGTH: 27
<212> TYPE: DNA
<213> ORGANISM: Artificial
<220> FEATURE:
<223> OTHER INFORMATION: Synthetic sequence from bacteria Yersinia
      pestis with a RGS tetra HIS tag

<400> SEQUENCE: 31

ctactcacac aatggcagca attgttg                                           27
```

TRANSFORMED *SACCHAROMYCES CEREVISIAE* ENGINEERED FOR XYLOSE UTILIZATION

CROSS-REFERENCE TO RELATED APPLICATIONS

This application claims the benefit under 35 U.S.C. 119(e) of U.S. provisional 61/101,399, filed Sep. 30, 2008, the contents of which are incorporated by reference herein.

BACKGROUND OF THE INVENTION

1. Field of the Invention

The invention is drawn to recombinant yeasts which are able to utilize xylose.

2. Description of the Prior Art

Over 95% of U.S. fuel ethanol is produced using corn. Eventually, it is envisioned that annual corn ethanol production can expand to 12-15 billion gallons, consuming 31% or more of the corn harvest. For this reason, commercializing lignocellulose as a feedstock for further ethanol production has been made a national priority. Despite a growing commitment by industry to move towards these more challenging feedstocks, technical barriers still remain unsolved. One critical need is for more robust microbial strains capable of fermenting the more diverse mixture of neutral sugars released by hydrolysis of lignocellulose. Plant cell wall lignocellulose contains, in order of relative importance, glucose, xylose, arabinose, galactose, and miscellaneous other sugars. While *Saccharomyces* strains ferment hexoses, they do not ferment the pentose sugars arabinose or xylose.

Several yeast, such as *Pachysolen tannophilus, Pichia stipitis*, and *Candida shehatate* naturally ferment xylose. While some of these are being pursued for commercialization, they have several defects, including the inability to grow anaerobically on xylose, low tolerance to acetic acid and other inhibitory chemicals common to biomass hydrolysates, and generally low productivity and yields compared to glucose-fermenting *S. cerevisiae*. Attention in recent years has turned to engineering bacteria to selectively produce ethanol (Dien at al., 2003), improving the performance of native xylose-fermenting yeast (Jeffries, 2006), or engineering *Saccharomyces* strains to ferment pentose sugars, especially xylose (Hahn-Hägerdal et al., 2007; Van Maris et al., 2006; Karhumaa et al., 2005; Kuyper et al., 2004 and 2005).

*Saccharomyces* yeast can naturally utilize the pentose phosphate pathway intermediate xylulose. Genetic strategies to enable the yeast to ferment xylose have centered on introducing the needed activities for converting xylose to xylulose. Naturally xylose-fermenting yeasts convert xylose into xylitol using xylose reductase (XR) and xylitol into xylulose using xylitol dehydrogenase (XDH), but the process gives rise to a cofactor imbalance that results in production of xylitol (Vran Mars et al., 2006; Kuyper et al., 2004). *Saccharomyces* yeast strains have been engineered that functionally express XR and XDH genes (Jeffries and Jin, 2004), and several have reasonable ethanol yields and reduced xylitol production, conceivably because enough oxygen enters the system to regenerate NAD+ from NADH via respiration instead of xylitol production (Karhumaa et al., 2005; Van Maris et al., 2006). Precisely controlled oxygen levels are nearly impossible to maintain in large-scale industrial operations, which limits the intermediate potential of these biocatalysts.

In an effort to convert xylose to xylulose without creating cofactor imbalances, *Saccharomyces* yeast strains were engineered to express a heterologous xylose isomerase (XI), which catalyzes this conversion directly (Karhumaa et al., 2005; Walfridsson at al., 1996). However the activity of the XI enzyme was too low for efficient xylose metabolism. It was discovered that the xylose isomerase from *Piromyces* sp. E2 can be expressed at sufficient levels in *S. cerevisiae* (Harhangi et al., 2003; Kuyper et al., 2004). After evolutionary engineering and expression of all genes for the enzymes involved in the conversion of xylose into intermediates of glycolysis in addition to expression of XI and deletion of the gene encoding aldose reductase, a *Saccharomyces* strain was constructed that had an ethanol production rate of 0.46 g per g xylose per hour under anaerobic batch cultivation on xylose. When grown on 20 g per liter glucose and xylose each, an exponential glucose consumption phase followed by a slower, almost linear, xylose consumption phase was observed (Kuyper et al., 2005). Further selection for xylose growth yielded a strain that when cultivated in anaerobic batch culture with 20 g per liter glucose and xylose each, fermented all sugars in 24 hours, an improvement of 20 hours over the strain before selection. On xylose alone it had an ethanol production rate of 0.49 g per g xylose per hour under anaerobic batch cultivation (Van Maris at al., 2006). Growth in anaerobic xylose cultures is considered a highly desirable quality in industrial fermentation since it reflects cell viability and increases the rate of ethanol production. Although uptake kinetics were also improved, the engineered *Saccharomyces* strains are only now moving towards commercialization (Hahn-Hägerdal et al., 2007). Co-fermentation of hexose and pentose sugars is still a major challenge.

SUMMARY OF THE INVENTION

We have now discovered recombinant *Saccharomyces cerevisiae* yeast that are capable of utilizing xylose. These recombinant *S. cerevisiae* are produced by transformation of the yeast with heterologous polynucleotide sequences coding for xylulokinase (XKS) from *Yersinia pestis* and xylose isomerase (XI). The transformants express these heterologous polynucleotides at a sufficient functional level to grow aerobically on xylose as the sole carbon source.

Surprisingly, further transformation of the recombinant yeasts to overexpress one or more of the *S. cerevisiae* polynucleotide sequences coding for PIP2, IMG2, MAK5, VPS9, COX10, ALE1, CDC7 or MMS4, permits the yeast to grow anaerobically on xylose as the sole carbon source. When grown under anaerobic conditions on a culture medium comprising both glucose and xylose, the transformed yeast exhibit increased production of ethanol, with the yeast growing on the xylose to increase their biomass and fermenting the glucose to ethanol.

In accordance with this discovery, it is an object of this invention to provide recombinant yeast that are effective for utilization of xylose.

Another object of this invention is to provide improved expression cassettes effective for transforming yeast wherein the resultant transformed yeast are effective for the utilization of xylose.

A further object of this invention is to provide improved recombinant yeast that are effective for use in the production of ethanol.

It is also an object of this invention to provide recombinant yeast that are genetically stable and maintain high ethanol production in an anaerobic environment.

Still another object of this invention to provide improved recombinant yeast that are effective for anaerobic growth and the fermentation of ethanol from hemicellulosic hydrolyzates containing glucose and xylose.

Other objects and advantages of this invention will become readily apparent from the ensuing description.

DEFINITIONS

Figure 1A:
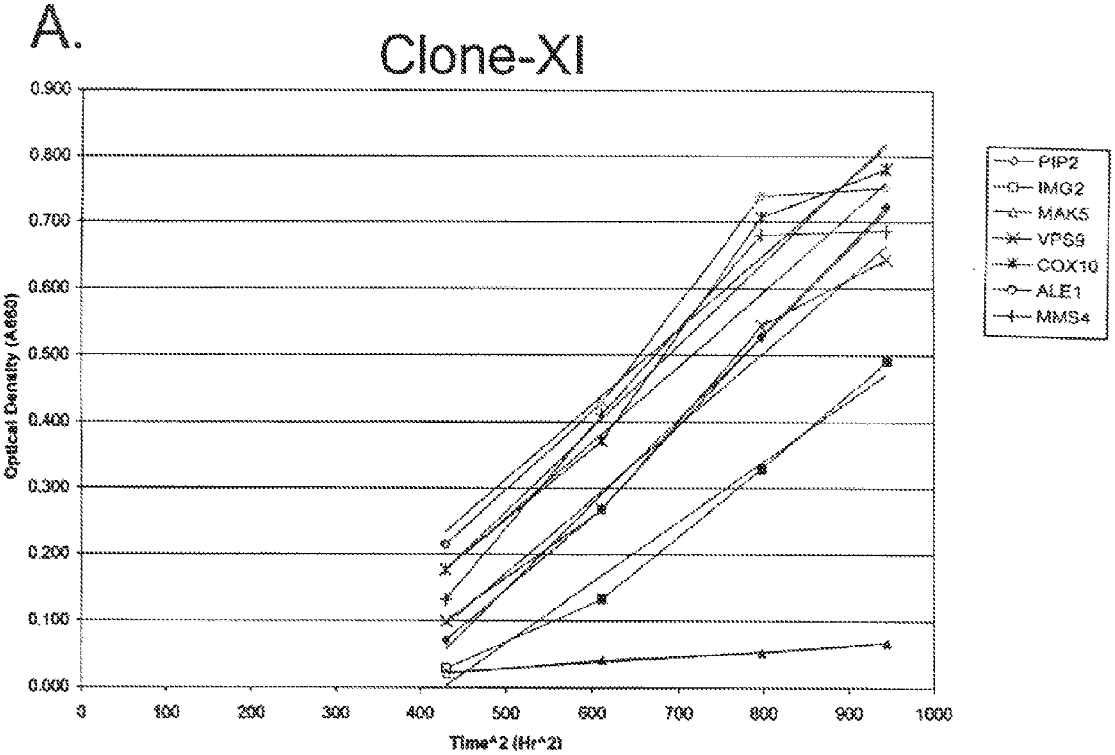
FIGS. 1A-1D show growth curves based on optical density at 660 nm of diploid strain cultures with and without expression of XKS in Example 3. Strains were grown on CM 2% glucose TRP LEU selective medium or on CM 2% xylose TRP LEU selective medium. A) Strains without XKS on glucose; B) Strains with XKS on glucose; C) Strains without XKS on xylose, D) Strains with XKS on xylose. NOTE: X-axis in xylose graphs covers longer timeframe than in glucose graphs and y-axis covers larger OD range in glucose graphs than in xylose graphs.
Figure 1B:
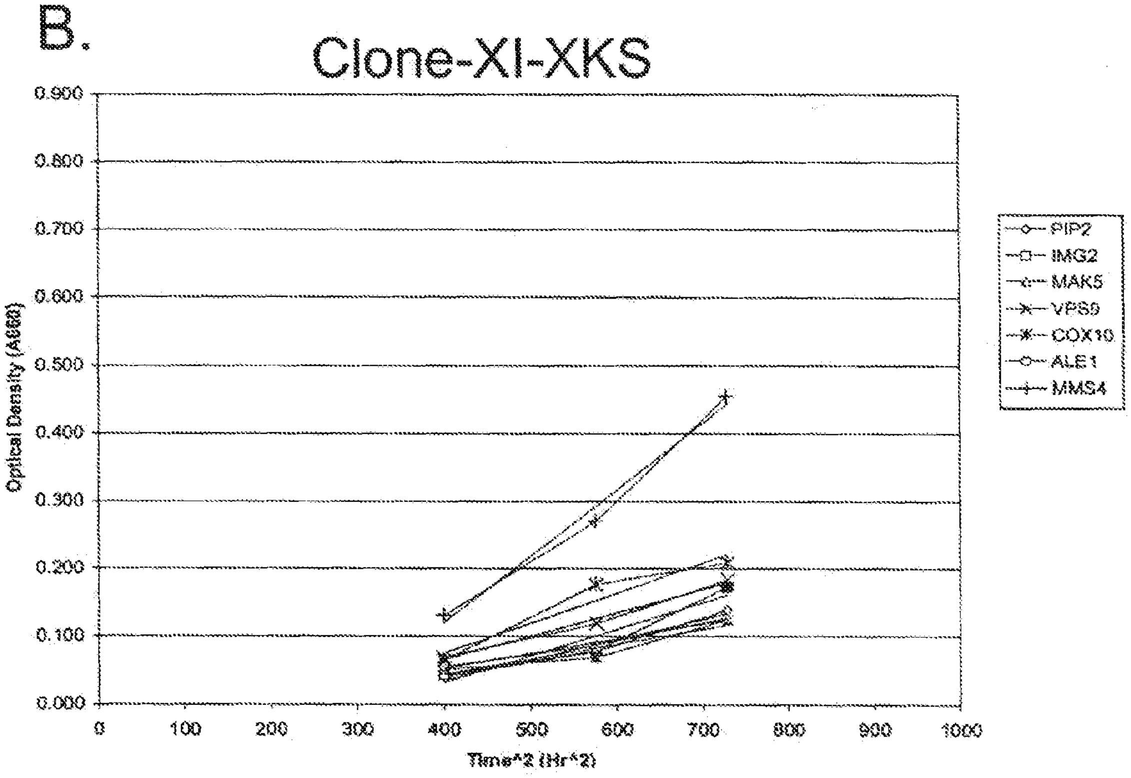
Figure 1C:
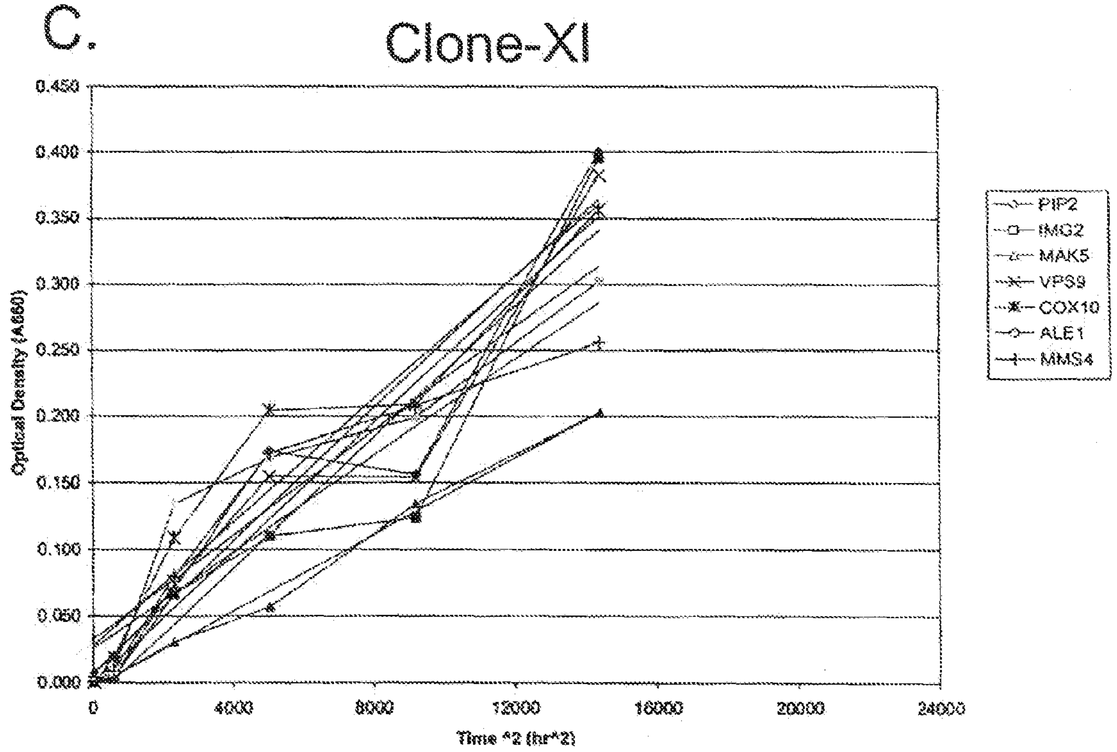
Figure 1D:
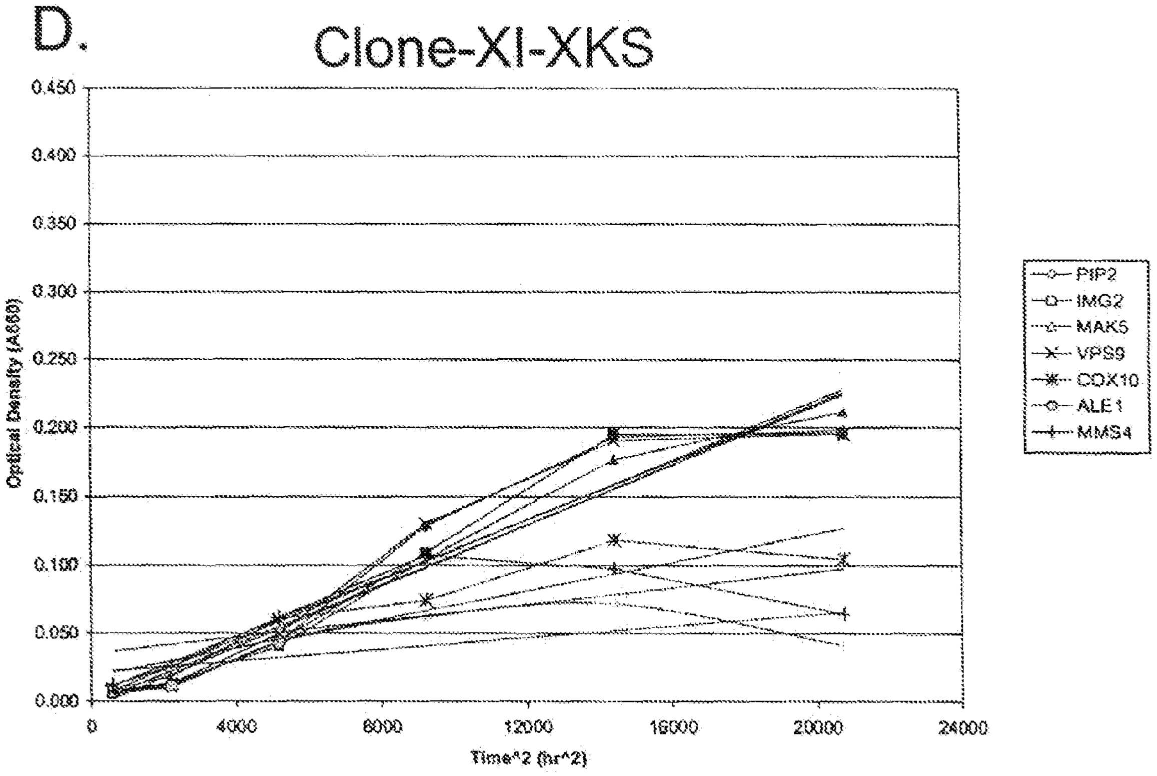

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or PNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine "T". The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant"

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In procaryotes and some fungi, for example, the exogenous DNA may be maintained on an episomal element such as a plasmid. With respect to most eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

Transformation of *Saccharomyces cerevisiae* with heterologous polynucleotide sequences coding for xylose isomerase (XI) and *Yersinia pestis* xylulokinase (XKS) confers the ability to utilize xylose as the sole carbon source with a very high growth rate (short doubling time) that is significantly greater than the parent *S. cerevisiae* yeast from which it was derived (lacking heterologous xylulokinase and xylose isomerase). *S. cerevisiae* transformed with XI and *Y. pestis* XKS exhibit aerobic growth on complete minimal (CM) xylose liquid medium at 30° C. (see Example 2) with a doubling time of 5.87 hours, approximately three times faster than the doubling time for aerobic growth on CM glucose liquid medium. The complete minimal (CM) medium formulation comprises: 0.13% Amino acid powder, 0.17% yeast nitrogen base, 0.5% $(NH_4)_2SO4$, 2.0% carbon source (i.e., glucose or xylose), and 2.1% agar. For selective medium the amino acid fraction has the designated amino acid (e.g. URA, TRP, or LEU) omitted or dropped out.

While the expression of XI and XKS enables the yeast to grow rapidly on xylose in an aerobic environment, this yeast does not grow anaerobically and fermentation rates are slow. The further transformation of the yeasts to overexpress one or more of the eight native *S. cerevisiae* polynucleotide sequences coding for transcription factor PIP2, mitochondrial ribosomal protein of the small subunit IMG2, essential nucleolar protein MAK5, vacuolar protein sorting VPS9, cytochrome C oxidase assembly protein heme A:farnesyltransferase COX10, lysophosphaoipid acyitransferase ALE1, DDK (Dbf-4-dependent kinase) catalytic subunit required for mitosis CDC7, or probable essential meiotic endonuclease MMS4, permits the yeast to grow anaerobically on xylose as the sole carbon source (note that PIP2 is the same as CDC7). The transformation and overexpression of these polynucleotide sequences in addition to XI and *Y. pestis* XKS allows the transformed yeast to grow rapidly on xylose as the sole carbon source under anaerobic conditions. In addition, the yet further transformation of the yeasts to overexpress the native *S. cerevisiae* polynucleotide sequence coding for fermentative alcohol dehydrogenase ADH1, further enhances the utilization of pentoses when expressed with XI, XKS, and COX10 as described by Hughes et al. (JALA, 2009, 14:200-212; and JALA, 2009, 14:190-199; the contents of each of which are incorporated by reference herein). Thus, the inclusion of both ADH1 and COX10 allows the transformed yeast to use pentose (i.e., xylose and arabinose) and hexose sugars to near completion, while producing greater amounts of ethanol than wild-type yeasts grown on cellulosic sugars, and is particularly preferred. These transformants grow anaerobically on xylose at a significantly greater rate than the parent *S. cerevisiae* yeast from which it was derived (not transformed with the above-mentioned PIP2, IMG2, MAK5, VPS9, COX10, ALE1, CDC7 or MMS4), exhibiting a doubling time of less than approximately 24 hours when cultured anaerobically on CM 2% xylose liquid medium at 30° C. When grown under anaerobic conditions on a culture medium comprising both glucose and xylose, these transformed yeast exhibit increased ethanol productivity, although no or little ethanol is produced from the xylose. Without wishing to be bound by theory, it is believed that xylose supports anaerobic yeast growth, with the yeast growing rapidly on the xylose to increase its biomass to high levels, and simultaneously fermenting the glucose nearly exclusively to ethanol.

Xylose isomerase and its corresponding gene which is suitable for use herein have been described previously and may be derived from a variety of heterologous sources. Although the E2 XI of *Piromyces* (Kuyper et al., 2003, the contents of which is incorporated by reference herein) is preferred, it is envisioned that the XI of *Clostridium, Thermocellum*, or *Bacillus subtilis* would also be suitable. The gene sequence and predicted amino acid sequence of the *Piromyces* XI enzyme was deposited in GenBank under GenBank Accession No. AJ249909 (the contents of which is incorporated by reference herein). In contrast, the source of the XKS is critical, and this enzyme is derived from *Yersinia pestis*. The gene coding sequence and predicted amino acid sequence of the *Y. pestis* XKS enzyme is described inn Example 1 and has been deposited in GenBank under GenBank Accession No. NP_671351 (the contents of which is incorporated by reference herein).

A recombinant xylose utilizing *Saccharomyces cerevisiae* yeast transformed with polynucleotide sequences coding for both *Piromyces* sp. E2 xylose isomerase and *Yersinia pestis* xylulokinase, designated INVSc1-XI-XKS and prepared as described in Example 1, has been deposited under the provisions of the Budapest Treaty in the Agricultural Research Service Culture Collection (NRRL), 1815 N. University St., Peoria, Ill., 61604, USA, on Mar. 19, 2009, and have been assigned Deposit Accession No. NRRL Y-50183. A second recombinant xylose utilizing *Saccharomyces cerevisiae* yeast, transformed with polynucleotide sequences coding for all of *Piromyces* sp. E2 xylose isomerase, *Yersinia pestis* xylulokinase, *S. cerevisiae* COCX10, and *S. cerevisiae* ADH1, and designated XI-XKS-COX10-ADH1::PJ69-4 (or GMAX) and prepared as described by Hughes et al. (JALA, 2009, 14:200-212, ibid), has been deposited under the provisions of the Budapest Treaty in the Agricultural Research Service Culture Collection (NRRL), 1815 N. University St., Peoria, Ill., 61604, USA, on Sep. 25, 2009, and have been assigned Deposit Accession No. NRRL Y-50328. This second recombinant xylose utilizing *Saccharomyces cerevisiae* yeast is capable of anaerobic growth and utilizing pentose (i.e., xylose and arabinose) and hexose sugars to near completion.

The polynucleotide sequences coding for the optional ADH1, PIP2, IMG2, MAK5, VPS9, COX10, ALE1, CDC7 and MMS4, are all derived from *S. cerevisiae*, and PIP2, IMG2, MAK5, VPS9, COX10, ALE1, CDC7 and MMS4 are described in Example 2. The polynucleotide sequences and predicted amino acid sequences for all of ADH1, PIP2, IMG2, MAK5, VPS9, COX10, ALE1, CDC7, and MMS4 have been previously deposited in GenBank and have been assigned NCBI Gene ID nos. 854068, 854545, 850434, 852439, 854876, 855931, 854346, 851545, and 850915, respectively. The contents of each of these NCBI Gene IDs are incorporated by reference herein.

It is also recognized that the process may utilize enzymes having at least 90%, preferably at least 95%, homology with the above mentioned amino acid sequences for the XI, XKS, ADH1, PIP2, IMG2, MAK5, VPS9, COX10, ALE1, CDC7 and MMS4, and sequences are still effective for their recognized functions.

Two polypeptides are said to be "identical" if the sequence of amino acid residues, respectively, in the two sequences is the same when aligned for maximum correspondence as described below, Sequence comparisons between two (or more) polypeptides are typically performed by comparing sequences of the two sequences over a segment or "comparison window" to identify and compare local regions of sequence similarity. Optimal alignment of sequences for comparison may be conducted by the local homology algorithm of Smith and Waterman (1981, Adv, Appl. Math., 2:482), by the homology alignment algorithm of Needleman and Wunsch (1970, J. Mol. Biol., 48:443), by the search for similarity method of Pearson and Lipman [1988, Proc. Natl. Acad. Sci. (U.S.A.) 85:2444], by, computerized implementations of these algorithms [(GAP, BESTFIT, FASTA, and TFASTA in the Wisconsin Genetics Software Package, Genetics Computer Group (GCG), 575 Science Dr., Madison, Wis.], or by inspection. "Percentage of sequence identity" is determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the which of comparison and multiplying the result by 100 to yield the percentage of sequence identity.

The term "substantial identity" of amino acid sequences for these purposes normally means sequence identity of at least 90%, and most preferably at least 95% compared to a reference sequence. The reference sequence herein is the predicted amino acid sequence of the XI, XKS, ADH1, PIP2, IMG2, MAK5, VPS9, COX10, ALE1, CDC7 and MMS4, referred to above. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The DNA sequences of the XI, XKS, ADH1, PIP2, IMG2, MAK5, VPS9, COX10, ALE1, CDC7 and MMS4 genes can be used to prepare recombinant DNA molecules by cloning into any suitable vector. Vectors used in practicing the present invention are selected to be operable as cloning vectors or expression vectors in the *S. cerevisiae* host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al. [Molecular Cloning: A Laboratory Manual, Cold Springs Harbor Laboratory, 1989] or Ausube et al. [Current Protocols in Molecular Biology, John Wiley & Sons, Inc, 1995], the contents of each of which are herein incorporated by reference, Further, the vectors may be non-fusion vectors (i.e., those producing the enzymes of the invention not fused to any heterologous polypeptide), or alternatively, fusion vectors (i.e., those producing the enzymes fused to a vector encoded polypeptide). The fusion proteins would of course vary with the particular vector chosen.

In accordance with a preferred embodiment, the vectors are the small ubiquitin-like modifier (SUMO) yeast expression vectors described by Butt et al. (U.S. Pat. No. 7,083,941), Butt et al. (U.S. patent application Ser. No. 10/504,785), Butt et al. U.S. patent application Ser. No. 11/794,532), Butt et al. (2005), and Malakhov et al. (2004), the contents of each of which are incorporated by reference herein. This vector system effectively allows the expression of numerous genes simultaneously. This plasmid system is preferably used for transformation and expression of both XI and XKS in *S. cerevisiae*, and may also be used for transformation and overexpression of one or more of the ADH1, PIP2, IMG2, MAK5, VPS9, COX13, ALE1, CDC7 or MMS4 genes. SUMO (Small Ubiquitin-Like-MOdifier) is about ~100 amino acid residue protein found in all eukaryotes. In eukaryotes, the C-terminus of SUMO is conjugated to epsilon amino groups of lysines of other proteins. SUMOylation of proteins is thought to compartmentalize proteins and protect them from degradation (Butt et al 2005). Fusion yeast SUMO (also called SMT3) has been shown to enhance the expression of recombinant proteins in *Escherichia coli* (Malakhov et al. 2004; Butt et al. 2005; Marblestone et al. 2006; Butt et al. U.S. Pat. No. 7,083,941; and Butt et al. U.S. patent application Ser.

No. 10/450,785). Fusion of human SUMO3 led to similar enhancement of protein expression in *E. coli* (Butt et al U.S. patent application Ser. No. 11/794,532). Prokaryotes do not contain SUMO or SUMO pathway enzymes. However, in eukaryotes such as yeast or mammalian cells, SUMO fusions are rapidly cleaved by de-SUMOylases to generate SUMO and native proteins. Remarkably fusion of wild type SUMO to poorly expressed proteins and its expression in eukaryotes also leads to enhanced expression of native protein (Peroutka et al. 2008). Thus SUMO, from yeast or human, enhances expression in prokaryotes and eukaryotes. The main difference is that in prokaryotes SUMO-fusions remain intact while in eukaryotes SUMO fusions are cleaved by endogenous de-SUMOylases to generate desired protein and SUMO. The yeast SUMO system has been used in this invention to generate lignocellulosic enzymes and to improve quality and quantity of XI, XKS and other target proteins.

Regardless of the specific vector utilized, various sites may be selected for insertion of the isolated DNA sequences. These sites are usually designated by the restriction enzyme or endonuclease that cuts them.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The nucleotide sequences comprising the XI, XKS, ADH1, PIP2, IMG2, MAK5, VPS9, COX10, ALE1, CDC7 and MMS4 genes may be inserted into the desired vector by known techniques. If, however, the vector is to serve as an expression vector, the vector should have a promoter, and the DNA sequences should be inserted in the vector downstream of the promoter and operationally associated therewith (that is, the promoter should be recognized by the RNA polymerase of the *S. cerevisiae* host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eucaryotic). Alternatively, any or all of the above control sequences may be ligated to the coding sequence prior to insertion into the vector.

DNA constructs may be introduced into the yeast host by numerous methods described in the technical and scientific literature. Transformation of yeast may be performed using standard techniques described in Maniatis et al., supra.

In general, linear or circular DNA constructs may be introduced into the host by techniques utilizing protoplast fusion, polyethylene glycol, liposomes, lithium acetate, electroporation, physical damage, biolistic bombardment, or *Agrobacterium* mediated transformation.

Successful transformants may be isolated by using markers, contained on the expression vectors, which confer a selectable trait to the transformed yeast host. These may include nutritional selection related to substrate utilization (such as, growth on acetamide containing medium) or prototrophy of a required growth product (such as, arginine, leucine, or uracil). Dominant selectable markers (such as, resistance to ampicillin, G418, hygromycin, and phleomycin) are also useful in selecting transformants that have taken up the introduced DNA construct.

The DNA construct may be replicated autonomously or integrated into the genome of the host. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

The recombinant yeast of this invention are effective for the fermentation of sugars from biomass or agricultural wastes to ethanol using conventional techniques. Many processes for the fermentation of monomeric sugars such as glucose generated from lignocellulose are well known, and are suitable for use herein. In brief, the cellulytic material may be enzymatically, chemically, and/or physically hydrolyzed to a glucose and xylose containing fraction. Alternatively, the recombinant *S. cerevisiae* of this invention may be further transformed with one or more genes encoding for enzymes effective for hydrolysis of complex substrates such as lignocellulose, and include but are not limited to cellulases, hemicellulases, peroxidases, laccases, chitinases, proteases, and pectinases. The glucose and xylose containing hydrolysate is then contacted with the recombinant yeast of this invention under anaerobic conditions effective for the growth of the yeast on the xylose to produce yeast biomass, and the fermentation of the glucose to ethanol. Details of the various fermentation techniques, conditions have been described, for example, by Wyman (1994) and Olsson and Hahn-Hagerdal (1996).

After completion of the fermentation, the ethanol may be recovered and optionally purified or distilled. Solid residue containing lignin may be discarded or burned as a fuel.

The following examples are intended only to further illustrate the invention and are not intended to limit the scope of the invention which is defined by the claims.

EXAMPLE 1

This invention describes that XI and XKS transformation of *S. cerevisiae* allows the strain to metabolize xylose efficiently as compared to wild type yeast. Expression of XI and XKS enables the yeast to grow rapidly on xylose in an aerobic environment. However, the strain does not grow anaerobically and fermentation rates are slow. A variety of selection methods and co-transformation of other yeast genes have lead to the development of a strain that metabolizes xylose much more efficiently. It is very likely that fast metabolizing yeast requires high level of protein expression that is not possible even under the control of strong glycolytic yeast promoters. To further improve the quantity and quality (catalytic function) of the proteins such as XI and XKS, we resorted to the use of SUNG fusion technology. As described herein, attachment of C-terminus of SUMO (yeast) to the N-terminus of poorly expressed protein dramatically enhances level of expression in prokaryotes and eukaryotes. To demonstrate that SUMO-fusion does impact the level of protein produced in *S. cerevisiae*, yeast strains were constructed that express XI with and with out SUMO fusion. The XI gene expression cassette, with and without SUMO, was integrated onto the yeast chromosome such that a single copy of the expression cassette was present. The western blot analysis of these strains allows us to determine the effect of SUNG fusion on the amount of XI produced in cells.

*Saccharomyces cerevisiae* strain PJ69-4 with genomically integrated *Piromyces* xylose isomerase (XI), with and without SUMO tags, were prepared as follows. To create an integrative plasmid, the yeast 2-micron origin of replication was deleted from the pSUMOduo/URA3/XI plasmid by the oligonucleotide-based QuikChange site-directed mutagenesis method (Stratagene). Subsequently, a SUMO-less version of the plasmid was made by deletion of the SUMO coding sequence by QuikChange mutagenesis, resulting in a construct coding for an N-terminal hexahistidine tag followed by a linker region (including the Gateway attB1 sequence and a NotI restriction site), a second His-tag, and then XI (MGHHHHHHGTSLYKKAGSAAAPFTMHHHHHH-xylose isomerase) (Sequence ID No. 1). Two His-tags are also encoded in the SUMO-containing parent plasmid (coding for MGHHHHHHG-SUMO-TSLYKKAGSAAAPFTMHHHHH-xyrlose isomerase) (Sequence ID No. 2). Once verified by sequencing, *E. coli*-derived plasmid minipreps of the two constructs were linearized with the restriction enzyme StuI, which cuts at a unique restriction site in the middle of the URA3 selectable marker, to direct plasmid integration to the URA3 locus of the yeast genome. To obtain yeast integrants, the linearized fragments were purified with a spin column and transformed into lithium acetate-treated, competent yeast cells (diploid strain PJ69-4, a uracil auxotroph with ura3-52 alleles), which were then grown on selective plates (synthetic complete yeast medium minus uracil; SC-ura) for two days at 30° C. Two individual colonies were then re-streaked on SC-ura media to obtain pure integrant colonies. These clones, which no longer require selection to maintain the *Piromyces* XI gene, were inoculated into YPD (yeast extract-peptone-dextrose) rich media and shaken overnight at 30° C.

Cells (10 ml culture) were grown to log phase and collected by centrifugation. The cell pellet was washed with water and suspended in 10 ml Tris-Hcl buffer pH 6.5, 1% SDS and mM beta mercaptoethanol, and boiled for 5 min. Equal amounts of protein were samples were resolved on denaturing 15% polyacrylamide gels with a 4% acrylamide stacking layer, Gels were transferred to Immoblin nitrocellulose (Millipore) using a Trans-Blot SD semidry transfer cell (Bio-Rad). After transfer, blots were blocked with 5% non-fat milk in PBS (pH 7.5)+0.05% Tween 20 (PEST) for 1 h. Following blocking, the blots were incubated in 1:1000 monoclonal Anti-His Antibody (Sigma) in PEST+milk for at least 1 h. Blots were washed with PEST three times and incubated with 1:2500 anti-mouse HRP conjugated antibody (Sigma) in PBST+milk for 1 h. Blots were again washed three times with PEST. HRP conjugates were detected with SuperSignal West Pico chemiluminescent substrate (Pierce) Blots were imaged using an LAS-3000 image analyzer (Fujifilm Life Science). Densitometry analysis was performed using Multi Gauge 3.0 software (Fujifilm Life Science). Density was calculated by measuring absorbance units (AU) by the image analyzer and by subtracting background and dividing by area. All areas compared were of equal size, while exposures were set to ensure that none of the bands compared had reached saturation. The software was then used to determine the relative amounts of various bands that correspond to XI (loaded on the same gel). Protein extract were prepared from a control strain that did not express XI. This lane was used acted as a control. Data is presented in a tabular form, Table 1.

As described above, in *S. cerevisiae* SUMO fusion proteins are cleaved by endogenous de-SUMOylases to generate SUMO and native proteins (XI). Since SUMO as well as XI contain 6-HIS tags we can easily detect the level of SUMO (calculated mol weight of SUMO is 10 KDa but it moves aberrantly around 20 Da in SDS-polyacrylamide gels) and XI (gel mobility ~50 KDa) present in cells by western blots, probed with 6-HIS antibody. Data from Table 1 shows that the level of XI increased about 10 fold in cells where XI was expressed as SUMO fusion. The yeast strain that contains a single copy cassette that expresses XI without SUMO fusion only showed a low level of expression. 6-HIS antibody also detected a His reactive band on the western blot that represent cleaved SUMO. As discussed above, SUMO fusions are cleaved in yeast to generate SUMO and native protein, and the higher level of SUMO reactive band in this strain confirms that increased level of XI is generated as part of SUMO fusion (see Table 1). Western blot analysis of proteins that were extracted from control yeast strain (not transformed with any expression vector or cassette) were run on the same gel did not show any 6-HIS reactive band in the respective mol weights, suggesting that the resultant band in yeast strains transformed with His-SUMO-XI and His-XI cassettes are the result of enhanced level of XI production. These data lays the foundation of invention and shows that one of the mechanisms is directly related to enhanced expression of XI, XKS and other genes when expressed as SUMO fusion. This mechanism is likely responsible for rapid anaerobic growth of yeast on lignocellulose and improved production of ethanol.

EXAMPLE 2

An automated strategy was used to produce yeast strains transformed with the three-vector plasmid system in this example. Step 1: Assembly of His-tagged xylose isomerase ORF and cloning into pSUMOduo/URA (vector 1). Step 2: Gene optimization using amino acid scanning mutagenesis (AASM) to randomize lycotoxin-1 at each of 25 positions for all 20 possible amino acids in the HisEntKLyt-1 fusion peptide and cloning into pSUMOduo/TRP (vector 2). Step 3: Cloning of additional genes important for xylose utilization into pSUMOduo/LEU (vector 3).

The three-plasmid yeast expression system utilizing the portable small ubiquitin-like modifier (SUMO) vector set (Butt et al. (U.S. Pat. No. 7,083,941); Butt et al. (U.S. patent application Ser. No. 10/504,785); Butt et al. (U.S. patent application Ser. No. 11/794,532); Butt et al., 2005; Malakhov et al., 2004), providing high expression levels, was used it to express a peptide of potential commercial value in a *Saccharomyces cerevisiae* strain also engineered to express xylose utilization and metabolic correction enzymes. The first SUMO vector expresses the xylose isomerase (XI) gene for pentose utilization. A value-added co-product is expressed with the second vector. The test product is the bioinsecticidal peptide, lycotoxin-1 (Lyt-1). The third vector expresses metabolic correction genes for pentose utilization. Engineering the yeast strain involved three steps. First, using a novel PCR assembly strategy we cloned the XI open reading frame (ORF) into the URA-selectable SUMO vector and placed it into the *S. cerevisiae* strain. Second, using amino acid scanning mutagenesis we generated a library of mutagenized Lyt-1 ORFs, cloned it into the TRP-selectable SUMO vector, and placed it into the XI-yeast. Third, the *Yersinia pestis* xylulokinase gene was cloned into the LEU-selectable SUMO vector and placed into the Lyt-1-XI-yeast. Yeast strains expressing XI and xylulokinase with or without Lyt-1 showed improved growth on xylose compared to XI-yeast.

Materials and Methods

Construction of pSUMOduo three-plasmid system for simultaneous expression of xylose isomerase, value-added products, and enzymes for metabolic corrections:

For the novel yeast episomal pSUMOduo high-level expression vector set, the protease-cleavable yeast small ubiquitin-related modifier (SUMO) tag (Smt3) was placed in front of an Invitrogen Gateway cassette, producing an AMP-selectable destination vector for recombination of library inserts. The SUMO insert ORFs were expressed behind an ADH promoter and also a T7 in vitro modified promoter. Three vectors were produced, pSUMOduo/URA, pSUMOduo/TRP, and pSUMOduo/LEU, each one having a different yeast selectable marker (for uracil, tryptophan, or leucine prototrophy, respectively) and each used to construct a plasmid to express a different ORF of interest: XI, toxin, or metabolic correction protein, simultaneously. The vectors contain the yeast high-copy 2μ origin of replication, to give a copy number of roughly 20 per yeast cell (Christianson et al., 1992).

The first plasmid pSUMOduo/URA was constructed as follows. First, a Gateway cassette fragment (Gateway Vector Conversion System, Invitrogen) containing attR1-ccdB-$Cm^R$-attR2 was amplified by PCR with primers containing BsI restriction sites designed to generate ACCT and GATC overhangs, then subcloned into BsaI/BamI-digested pSUMO (aka pET24-6×His-SUMO) (Malakhov et al., 2004) to construct the plasmid pSUMO-Gate way. A $P_{T7}$-$His_6$-Smt3-Gateway cassette-$T_{T7}$ fragment was then PCR-amplified from pSUMO-Gateway, digested with EcoRV and BbsI to generate a blunt end and a GATC overhang, and subcloned into a SmaI/Bg1II fragment of pRS306-$P_{ADH}$ (Sterner et al., 1999), containing the *E. coli* $amp^R$ marker, the yeast URA3 marker, and the promoter of the yeast ADH1 gene. The resulting plasmid was digested with SapI and ligated with a SapI fragment from pRS426 (Christianson et al., 1992) containing the yeast 2μ origin of replication. QuikChange mutagenesis (Wang and Malcolm, 1999) was then used on the resulting plasmid to delete two extraneous, tandem $P_{T7}$ sequences present in the vector backbone from the previous construction of pRS306-$P_{ADH}$ (Sterner et al., 1999).

To replace the URA3 selectable marker in pSUMOduo/URA with either TRP1 or LEU2 and create the other 2 vectors of the 3-vector system, the TRP1 sequence was amplified from pGBKT7 vector (Clontech) with oligos 82 (CGCGAGCTAGCCGCGCGTTTCGGTGATGACGGTGA) (Sequence ID No. 3) and 83 (CGCGACGCGTGATCGGCAAGTGCAAAACAATACT (Sequence ID No. 4) and LEU2 was amplified from pGADT7 vector (Clontech) with oligos 85 (CGCGACGCGTTTAACCAAGGTGGATTTTCTTTTAACTTCT) (Sequence ID No. 5) and 509 (CGCGAGCTAGCCGACTGGAAAGCGGGCAGTGAGCGCA) (Sequence ID No. 6). Inserts were then digested with NheI and MluI and cloned into similarly digested pSUMOduo/URA vector.

Assembly of Xylose Isomerase Open Reading Frame and Production of pSUMOduo;/URA/HisXI-INVSc1 Yeast Strain:

The *Piromyces* sp. E2 xylose isomerase (XI) gene sequence (GenBank Accession No. AJ249909) (Kuyper et al., 2003) was used to synthesize oligonucleotides for assembly into the XI open reading frame (ORF) that was placed directionally in the expression vector pSUMOduo/URA. Oligos A to R used in the gene assembly protocol adapted for the automated robotic platform are listed in Table 2, and designated Sequence ID Nos. 7-24, respectively. In the first step of the assembly of the XI ORF, section 1 forward oligo (B) was annealed to section 2 reverse oligo (C) and filled in with dNTP using the ABI high-fidelity Taq kit as previously described (Hughes et al., 2005). PCR reactions were carried out using the same ABI kit with the forward primer (A) to enhance production of this small amplicon as the first section (1-2) of the XI gene assembly. This amplicon was purified using a modified GENECLEA II kit (Qbiogene). The purified eluted amplicon was TOPO cloned into pENTR D TOPO and the resulting reaction was transformed into TOP 10 competent bacterial cells as described previously (Hughes et al., 2006). The colonies were picked, grown on selective LB KAN 25 plates and a plasmid preparation was produced. The plasmids were restricted with BsrGI and the XI section 1-2 insert was verified at 199 bp. This pENTR D TOPO XI section 1-2 plasmid preparation was then used as a template in production of the section 1-2-3 amplicon in the same ABI high fidelity PCR reaction using the same short forward oligo primer (A) and XI section 3 long reverse oligo (D). The PCR amplicons were purified and TOPO cloned into pCR8 TOPO. The resulting plasmids were transformed into TOP 10 cells that were recovered and selected on LB SPEC 100 plates (Teknova). The plasmid preparations from colonies picked from these SPEC 100 plates were restricted and the XI section 1-2-3 insert verified at 250 bp. The resulting plasmid pCR8 TOPO XI section 1-2-3 was used as a template in the next gene assembly PCR step with the same primer (A) and XI section 4 long reverse oligo (E). The resulting PCR reaction product was purified, TOPO cloned into pENTR D TOPO vector, and transformed into TOP 10 cells that were recovered and selected on LB KAN 25 plates (Teknova). Plasmid preparations from colonies picked from these KAN 25 plates were restricted and the XI section 1-2-3-4 insert at 318 bp was sequence verified. The resulting pENTR B TOPO XI section 1-2-3-4 plasmid was then used as template in the next PCR gene assembly step with short forward oligo primer (A) and XI section long reverse oligo (F), followed by purification, cloning, transformation, and selection. The process was repeated with each subsequent section long reverse oligo (G to R), alternating between cloning into pENTR D TOPO and pCR8 TOPO vectors in order to isolate only those vectors containing inserts with the newly added section via SPEC or KAN selection, but not select the previous template.

This final plasmid pCR8 TOPO XI section 1-17 was used in a polishing PCR reaction with the short forward oligo (A) and the short reverse oligo FBTHTS 6-20-04EE OLIGO 5'TTAACTACGATTAACTTATTGGTAC3' (Sequence ID No. 25) to generate the full xylose isomerase wild-type ORF (Kuyper et al., 2003) with His tag. The resulting purified, polished amplicon was placed into pENTR D TOPO, cloned into vector 1 of the 3-vector system, the pSUMOduo/URA (LifeSensors, Malvern, Pa.), and transformed as described previously (Hughes et al., 2005) into INVSc1 yeast (Invitrogen), a fast growing diploid strain ideal for expression, that does not sporulate well, and carries the mutations MATa his3D1 leu2 trp1-289 ura3-52, to produce the strain pSUMOduo/URA/HisXI-INVSc1 (or INVSc1-XI).

Production of pSUMOduo/TRP/HisLyt-1 Mutant Library and Transformation into INVSc1-XI Strain:

The pENTR D TOPO library of ORFs for mutant lycotoxin-1 sequences produced by amino acid scanning mutagenesis (AASM) from clone #59 as described previously (Hughes et al., 2007) was placed into vector 2, pSUMOduo/TRP, of the 3-vector system (LifeSensors, Malvern, Pa.). The library was designed to code for all possible 20 amino acids at each of the 25 amino acid positions in the clone #59 variant of lycotoxin-1 peptide (GenBank Accession No. P61507) from wolf spider *Lycosa carolinensis* (Yan and Adams, 1998). This set of multiplexed ORF inserts in pENTR D TOPO was moved by LR clonase into the pSUMOduo/TRP vector to produce the pSUMOduo TRP/HisLyt-1 AASM library. This was mass transformed on the automated robotic platform into the INVSc1-XI strain to produce pSUMOduo/URA/HisXI-pSUMOduo/TRP/HisLyt-1 AASM-INVSc1 (or INVSc1-XI-Lyt-1) strains in each of 25 multiplexed wells, one well per amino acid position mutation, with all 20 amino acid possibilities for that position in each well (Hughes at al., 2007 and 2008)

Transformation of INVSc1-XI-Lyt-1 Yeast Strains with Xylulokinase or Transaldolase Gene:

To further enhance growth on xylose, the xylulokinase gene or the transaldolase gene from *Yersinia pestis* was placed in the third vector, pSUMOduo/LEU, of the 3-vector system and transformed as described previously (Hughes et al., 2005, the contents of which are incorporated by reference herein) into the yeast strain carrying the other 2 plasmids, pSUMOduo/URA/HisXI-pSUMOduo/TRP/HisLyt-1 AASM-INVSc1. The xylulokinase ORF (GenBank accession No. NP_671351) was moved from pDONR221 (Zuo et al., 2007) via LR clonase into pSUMOduo/LEU to generate the plasmid pSUMOduo/LEU/XKS, which was then transformed into the 2-plasmid INVSc1-XI-Lyt-1 strain to produce the strain pSUMOduo/URA/HisXI-pSUMOduo/TRP/HisLyt-1 AASM-pSUMOduo/LEU/XKS-INVSc1 (or INVSc1-XI-Lyt-1-XKS). A second strain was generated in which the transaidolase ORF (GenBank Accession No. NP_671009) was moved from pDONR221 (Zuo et al., 2007) via LR clonase into pSUMOduo/LEU to generate the plasmid pSUMOduo/LEU/TAL. This plasmid was transformed into the 2-plasmid INVSc1-XI-Lyt-1 strain to produce the strain pSUMOduo/URA/HisXI-pSUMOduo/TRP/HisLyt-1AASM-pSUMOduo/LEU/TAL-INVSc1 (or INVSc1-XI-Lyt-1-TAL)

Polyacrylamide Gel Electrophoresis and Western Blot Procedures:

Transformed yeast strains carrying the pSUMOduo plasmids, each with a different selectable marker, were inoculated into 1.0 mL of the respective selective medium and grown 2 days at 30° C. in deepwell plates. The resulting cultures were spun down at 4,000 rpm for 20 min in a swinging bucket centrifuge with plate carriers, the supernatant was discarded, and the pellet in the first well of the first column of the plate was resuspended by vortexing with 250 μL Y-PER lysis buffer. This solution was used to resuspend the pellets in each successive well of the first column. The solution was transferred to the first well of the next column and vortexed to resuspend the pellet. The process was repeated until all the pellets were combined and resuspended in the last well of the last column. This 250 μL sample was pipetted into a 1.5 mL tube and incubated at 4° C. with rotating for 3-4 hours. A 30-μL aliquot from this tube was pipetted into the wells in a Hard-Shell 96-well plate (Bio-Rad) and 30 μL of 2× tris-glycine SDS loading buffer (Invitrogen) with beta-mercapto-ethanol (BME) were added to each well. To the remaining 220 μL of sample in the 1.5 mL tube were added 100 μL of Super Flow Ni beads (Qiagen), and the sample incubated at 4° C. with rotating for approximately 3 hours. The sample was centrifuged at 13,000 rpm for 2 min and ML of the supernatant was pipetted into a new 1.5 mL tube. Thirty μL of 2× tris-glycine SDS loading buffer with BME were added. These samples and the samples in the Hard-Shell plates were heated to 95° C. for 10 minutes, loaded onto 1.5-mm thick 16% tris-glycine 15-well SDS-PAGE gels (Invitrogen), and run at 110V for 150 min. The gel was assembled into an X-Cell® Novex box and run in 1× tris glycine running buffer. It was removed and transferred to PVDF cut sheets (Invitrogen). The transfer took place in the Novex transfer apparatus with 1× transfer buffer (Invitrogen) for 10 hours at a constant 200 mA, Westerns were chromogenic and performed with the Western Breeze kit (Invitrogen) according to the manufacturer's directions using a Qiagen Penta-His antibody resuspended in 1 mL of 1×PBS with magnesium and calcium (secondary antibody was anti-mouse antibody) Western blot images were captured using the Alpha Innotech 3400. The Alpha Innotech 3400 was also used to analyze Western blot images of the cell lysates for the amount of His-tagged protein expressed. The AlphaEaseFC software for spot density measurement for Windows 2000 was used to determine band density compared to known molecular weight markers from the Qiagen 6×His-tagged set treated in the same fashion as the samples on the gels.

Coomassie Gel Analysis of Ethanol Wash of Cell Surface and Ethanol Extraction of Cell Lysate:

The INVSc1-XI strain and the strains expressing variants C3 and C6, INVSc1-XI-Lyt-1-C3 and INVSc1-XI-Lyt-1-C6, were grown 4 days at 30° C. in 25 mL CM xylose respective selective media in a shake flask. Two mL were pelleted and the pellets were treated with ethanol to a final ethanol:cell pellet ratio of 5:1. The ethanol washes were recovered and air dried. Twenty μL of 2× tris-glycine loading buffer were added. The washed cells were then treated with 50 μL of Y-PER solution, vortexed vigorously, and added to 50 μL of 2× tris-glycine SDS/BME loading buffer. The ethanol wash samples and the cell lysate samples were heated to 95° C. for 5 minutes, allowed to cool, and loaded onto 1.5-mm thick 16% tris-glycine 15-well SDS-PAGE gels (Invitrogen), and run at 110V for 60 min. The gels were stained with Simply Blue stain (Invitrogen) for 1 hour and de-stained with water for 10 hours. The resulting gels were imaged and analyzed using the Alpha Innotech 3400 (as for Western blot gels above).

Transmission Electron Microscopy;

The yeast strain sample was collected on a 200 mesh, nickel, Formvar coated grid. The grid was placed on the specimen drop for 5 min, then washed gently with water and drained. The grid was negatively stained by placing it, membrane side down, onto a drop of 2% aqueous uranyl acetate for 2 min. The sample was scanned and photographed using a JEM 100C Transmission Electron Microscope (JEOL).

Scanning Electron Microscopy:

Yeast cells from the plate were suspended in saline (0.85% NaCl) and centrifuged to remove residual medium. Following a modified procedure of Bang and Pazirandeh (1999), the cell pellet was suspended and fixed in 2.5% glutaraldehyde prepared in 100 mM cacodylate buffer, pH 7.2, for one hour on ice. To remove remaining glutaraldehyde, the cells were rinsed with the buffer twice and then with distilled water once, allowing several minutes for each step. The cells were dehydrated, respectively, in solutions containing 50%, 70%, 80% and 100% ethanol successively for 15 minutes for each treatment. Cells were mounted on the aluminum stub and placed in the desiccator to dry overnight or until needed. The samples were subjected to scanning electron microscopy and analysis (Zeiss Supra 40 VP)

Light Microscopy and Immunofluorescent Microscopy:

Selected colonies from plates containing each of the yeast strains, TNhVSc1, INVSc1-XI, and INVSc1-XI-Lyt-1 (variants C3, A6, B9, and C6), were inoculated into 1 mL of the appropriate liquid media in a 96-well deepwell plate and grown for 48 hours at 30° C. on an incubator shaker. The resulting cultures were pelleted at 300 rcf for 3 minutes in an Allegra X12R centrifuge at room temperature, and the supernatant was removed. The pelleted cells were resuspended by adding 500 μL of PBS pH 7.4 buffer per well. Pelleting and resuspension were repeated twice. Cells were fixed using 1 mL per well of a non-toxic 'Prefer' fixative solution (Anatech LTD), incubated for up to 2½ hours at room temperature, washed again, and then subjected to staining.

In addition, prior to fluorescence staining, cells from each of the same yeast strains were digested using Zymolyase enzyme (Biosciences or MP-Biomedicals), which lyses cell walls and allows entry of large dyes into the cell interior. Cells were incubated in 500 μL of PBS buffer with a '25 unit' concentration of active enzyme (e.g., 5 μL of 1 mg/mL (1%) zymolyase stock) for a maximum of 45 minutes at room temperature. After digestion, the cells were pelleted, washed twice to remove the zymolyase, and resuspended in a dye solution.

Nuclear staining of undigested and digested yeast cells was carried out using DAPI dye (1/500$^{th}$ dilution of 0.1 mg/mL stock solution). Location of expressed His-tagged proteins was determined using a Penta-His Alexa Fluor 532 anti-H is antibody conjugated dye (Qiagen, CA). The Alexa Fluor dye was prepared (1/100th dilution of 200 g/mL stock solution) in a blocking buffer containing 5 mg/mL BSA to reduce non-specific staining. Approximately 100 μL of dye solution was added per well and incubated up to 1½ hours at room temperature followed by a single wash step and resuspension in 500 μL PBS buffer. Dilute suspensions of cells (approximately 200 μL; OD 600 below 0.2) were loaded into a flat-bottom 96-well plate (ThermoFisher Scientific) prior to imaging.

Brightfield and fluorescence images were taken using the BioRyx 200 platform (Arryx Inc) with the Nikon TE2000 microscope appropriately modified to accommodate flat-bottom 96-well plates and collect images from the center of each well using automated stage movement (Prior Scientific), a 40× Nikon air objective (NA=0.95), a Retiga EXi camera (Qimaging), and LabRyx Software.

For stained cells, 'blue' fluorescence was collected from the DAPI dye using a Nikon UV-2A fluorescence cube (excitation: 355 nm, 50 nm bandwidth, emission: 420 nm, LP) and 'red' fluorescence was collected from the antibody-based Penta-His Alexa Fluor 532 conjugate dye using a Nikon Cy3 HYQ fluorescence cube (excitation: 545 nm, 30 nm bandwidth, emission: 610 nm, 75 nm bandwidth). Exposure times were 10 milliseconds for brightfield and 1 second for fluorescence with minimal offset and gain. A series of sequential images were taken for each sample (brightfield, 'blue', and 'red') and composite (overlay) images were created for analysis.

Aerobic and Anaerobic Growth on Selective Media Plates and in Liquid Media:

For growth on glucose (2.0%), samples were streaked on complete minimal (CM) glucose URA selective plates for the pSUMOduo/URA/HisXI-INVSc1 yeast strain, on CM glucose-URA/TRP selective plates for the pSUMOduo/URA/HisXI-pSUMOduo/TRP/HisLyt-1 AASM-INVSc1 yeast strains and on CM glucose URA/TRP/LEU selective plates for the pSUMOduo/URA/HisXI-pSUMOduo/TRP/HisLyt-1 AASM-pSUMOduo/LEU/XKS (or TAL)-INVSc1 yeast strains. For growth on xylose (2.0%), similar plates were used but CM xylose was substituted for CM glucose. The complete minimal (CM) medium formulation comprises: 0.13% Amino acid powder, 0.17% yeast nitrogen base, 0.5% $(NH_4)_2SO4$, 2.0% carbon source (i.e., glucose or xylose), and 2.1% agar. For selective medium the amino acid fraction has the designated amino acid (e.g. URA, TRP, or LEU) omitted or dropped out. For aerobic growth, the plates were placed into an NBS 4230 incubator (New Brunswick Scientific) at 30° C. For anaerobic growth, the plates were first placed in an anaerobic chamber for at least 2 hours and then samples were applied. The plates were wrapped and placed back into the anaerobic chamber for 6 days. Anaerobic conditions are maintained using BD GasPak EZ Gas Generating Container Systems with Indicator (Becton Dickinson). The GasPak is a paper sachet containing inorganic carbonate, activated carbon, ascorbic acid and water. When the sachet is removed from its outer packaging it becomes activated by exposure to air and rapidly reduces the oxygen content in the chamber, while the inorganic carbonate produces carbon dioxide. The BBL 150 System uses 3 sachets. The sachets are opened and placed in the chamber, the lid is secured, and the system is placed in the incubator for 24-48 h at 35° C. Sachets produce an anaerobic atmosphere, with greater than 15% carbon dioxide, within 24 h. After 20 minutes, visible condensation is present on the inside of the container. Pictures of all plates were taken digitally. Cultures were grown for 2 days, diluted 10,000 fold in sterile water, then 100 μL were spotted onto the respective plates and allowed to grow 3 days to generate a yeast colony. For growth in liquid medium, the samples were inoculated into a flask containing the appropriate selective medium.

Results

Yeast Strain Produced Using 3-Plasmid Yeast Expression Technology:

The pSUMOduo high-copy expression vector set, containing the protease-cleavable yeast SUMO tag (Smt3) behind an ADH promoter and also a T7 in vitro modified promoter, consists of three vectors, pSUMOduo/URA, pSUMOduo/TRP, and pSUMOduo/LEU, each one having a different yeast selectable marker. Three plasmids were constructed and placed into INVSc1 yeast, a fast growing diploid strain that carries the mutations MATa his3D1 leu2 trp1-289 ura3-52, to take advantage of the ability of the *S. cerevisiae* to metabolize xylose into xylulose (Kuyper et al., 2003, 2004, and 2005). The yeast strain engineered with these plasmids expressed 1) the PCR assembled xylose isomerase ORF, 2) the library of mutagenized lycotoxin-1 ORFs, and 3) genes for either of two important pentose phosphate pathway enzymes for metabolic correction to enable the yeast to utilize xylose more efficiently. The assembly of the xylose isomerase ORF was performed using a robot-adapted strategy that involved production of increasingly longer templates with long oligonucleotide additions to the end of the previous section of the sequence, alternating between cloning into pENTR D TOPO with the KAN selectable marker and pCR8 TOPO with the SPEC selectable marker to ensure the previous template was not selected. For each of the TOPO cloning steps a fragment was always produced and at least one clone was always obtained. The pENTR D TOPO plasmid with the complete xylose isomerase ORF was cloned into the yeast high-copy expression vector pSUMOduo/URA and transformed into the INVSc1 yeast strain to produce the pSUMOduo/URA/HisXI-INVSc1 (or INVSc1-XI) yeast strain. A large library of mutagenized wolf spider lycotoxin-1 ORFs that was produced by amino acid scanning mutagenesis from lycotoxin-1 clone #59 (also called C3) on the automated robotic platform as described previously (Hughes et al., 2007) was placed in the second SUMO vector to express toxin variants optimized for lethality to a test insect pest. The resulting library was transformed into the INVSc1 yeast already containing the SUMO expression plasmid for xylose isomerase to produce pSUMOduo/URA/HisXI-pSUMOduo/TRP/HisLyt-1AASM-INVSc1 (or INVSc1-XI-Lyt-1) yeast strain. To improve xylose utilization by the yeast strain, an additional open reading frame, for either xylulokinase or transaldolase, was placed in the third SUMO vector, pSUMOduo/LEU, and the resulting plasmid used to produce the pSUMOduo/URA/HisXI-pSUMOduo/TRP/HisLyt-1 AASM-pSUMOduo/LEU/XKS (or TAL)-INVSc1 [or INVSc1-XI-Lyt-1-XKS (or TAL)] yeast strains. Overexpression of these enzymes is suggested as a means of enabling yeast to metabolize xylose more rapidly through the pentose phosphate pathway (Jin et al., 2003; Kuyper et al., 2004 and 2005; Van Maris et al., 2007).

Results of XI Expression in INVSc1-XI Yeast:

A transmission electron micrograph of the INVSc1-XI yeast strain compared to that of the INVSc1 yeast strain grown aerobically on CM glucose plates shows that the XI-yeast is expressing large amounts of additional material in comparison to the strain without the XI plasmid. As a result, the shape of the cell is changed from balloon-shaped to almost cube-shaped with a dent in the center. The growth of the INVSc1-XI yeast strain on CM glucose URA selective plates and in CO glucose URA selective liquid medium was compared to growth of the strain on CM xylose URA selective plates and CM xylose URA selective liquid medium. Yeast expressing XI grew well aerobically both on CM glucose URA selective plates and in CM glucose URA selective liquid medium. It grew aerobically to a very limited extent on CM xylose URA selective plates after 2 days, but it did not grow in CM xylose URA selective liquid medium. The Western gels for both the cell lysates (left) and for the Ni bead-purified cell lysates (right) show a strong attB1His-XI band at 53.7 kD and a 16.6 kD band corresponding to the 6×HisSUMO fragment in the INVSc1-XI yeast strain. These bands are absent in the lanes corresponding to the INVSc1 yeast strain. The light microscope images of the INVSc1-XI yeast strain also show changes in the shape of the cells compared to the INVSc1 strain in agreement with the TEM images. The strong staining seen in the immunofluorescent images of the digested cells in the INVSc1-XI yeast strain confirm the expression of His-tagged proteins, HisXI and HisSUMO; no staining is seen in the cells of the INVSc1 yeast strain.

Expression and Analysis of Lycotoxin-1 Variants:

The doubling times of INVSc1-XI-Lyt-1 (variants C3, A6, B9, C6) yeast strains grown aerobically in CM glucose URA/TRP selective liquid medium are presented in Table 3. Growth on CM glucose liquid medium for the strains expressing the lycotoxin-1 variants is normal, with doubling times the same as that for the XI yeast strain without Lyt-1. No growth is seen for the INVSc1-XI-Lyt-1 strains in CM xylose URA/TRP selective liquid medium.

Figure 3:
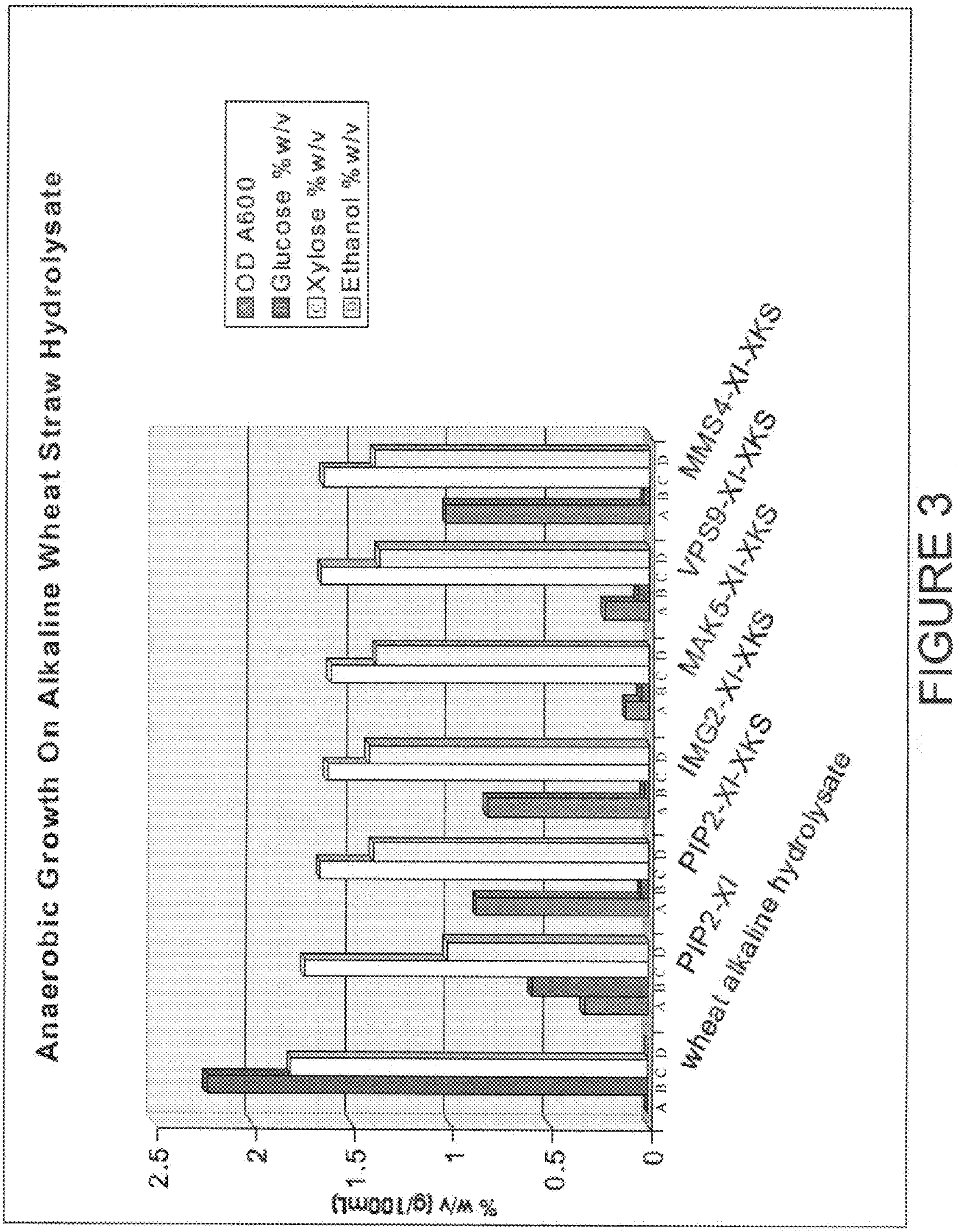
FIG. 3 shows the maximum amounts of ethanol from double-plasmid (XI-Clones) and triple-plasmid (XI-Clones-XKS) diploid PJ69-4 yeast strains that gave optimum growth on alkaline hydrolysate and the xylose, and glucose levels after 100-hour incubation in 25 mL hydrolysate of Example 3. Optical density at 600 nm is also shown.

The INVSc1-XI-Lyt-1 yeast strains were also examined under a light microscope and by using immunofluorescent microscopy (FIG. 3). The light microscope images show more extensive shape changes than seen for the INVSc1-XI strain. The immunofluorescent images demonstrate increased staining of expressed His-tagged proteins, HisXI, HisLyt-1, and HisSUMO from both vectors, in the undigested INVSc1-XI-Lyt-1 yeast cells (more for A, B9, and C6 than C3) compared to the undigested INVSc1-XI yeast strain. When the permeability of the cells is increased with zymolyase to allow immunostaining of His-tagged expressed proteins in internal locations of the cells, the INVSc1-XI-Lyt-1 strains, particularly A6, show intense spots within the cell interior.

Analysis of Strains Expressing Metabolic Correction Enzymes:

The doubling times of INVSc1-XI-Lyt-1 (variants C3, A6, B9, or C6)-XKS (or TAL) yeast strains grown aerobically in CM glucose or CM xylose URA/TRP/LEU selective liquid medium and of the INVSc1-XI strain grown aerobically in CM glucose URA selective liquid medium are presented in Table 3. Aerobic growth in CM glucose for the strains expressing the lycotoxin-1 variants and the metabolic correction enzymes is normal, with doubling times very close to that for the INVSc1-XI yeast strain.

An INVSc1 strain expressing XI and XKS used as a control shows aerobic growth in CM xylose URA/LEU selective liquid medium with a doubling time approximately three times that of aerobic growth in CM glucose liquid medium. Strains expressing Lyt-1 variants C6 or C3 in addition to XI and XKS also show aerobic growth in CM xylose liquid medium but with doubling times 2 to 3 times longer, respectively, than that for the INVSc1-XI-XKS control strain. However, strains expressing Lyt-1 variants A6 or B9 in addition to XI and XKS show essentially no growth in CM xylose liquid medium. In our hands, no growth was seen in CM xylose liquid medium for the control strain expressing only XI and TAL (data not shown), for strains expressing XI and the Lyt-1 variants, or for strains expressing XI, the Lyt-1 variants and TAL (Table 3).

Western blot analysis of the INVSc1-XI-Lyt-1 and INVSc1-XI-Lyt-1-XKS (or TAL) strains using penta-His antibody demonstrates that all strains are expressing a lycotoxin-1 species and xylose isomerase. Lysates prepared after growth on CM glucose URA/TRP or URA/TRP/LEU selective plates and run directly on a 16% polyacrylamide gel show three major bands for all 12 strains, at 53.7 kD for the attB1HisXI recombinant protein, at 16.6 for the HisSUMO tag removed from HisXI, HisLyt-1 and XKS or TAL by yeast SUMO protease 1, and at 10.7 kD for the attB1HisEntKLyt-1 toxin band. Lysates prepared after growth on CM glucose URA/TRP or URA/TRP/LEU selective plates and subjected to Ni bead purification of the His-tagged proteins, then run on a 16% polyacrylamide gel, show the same 3 bands and an additional band at 21.4 kD, attributed to a dimer of the attB1HisEntKLyt-1 protein. The concentration of His-tagged protein in each band for XI and for XI and Lyt-1 was calculated using AlphaEaseFC software for Windows 2000 to determine band density compared to known molecular weight markers from the Qiagen 6×His-tagged set treated in the same fashion as the XI and Lyt-1 samples. The results are shown in Table 4. Protein concentrations for the individual XI and Lyt-1 bands for the 2-plasmid strain are on the order of 12 to 14 μg. For the 3-plasmid strain, expression of Lyt-1 is slightly greater than that of XI, with the Lyt-1 concentrations ranging from 14 to 19 μg and the XI concentrations from 9 to 12 μg. However, the sum of the concentrations determined for the XI and Lyt-1 bands is similar in all strains expressing them, about 25 to 29 μg. The concentrations of XKS and TAL cannot be determined directly since they are not His-tagged, but the increased concentration of the His-tagged SUMO band (14 to 16 μg) in the triply transformed yeast strains over that in the doubly transformed yeast strains (8 to 9 μg) gives a measure of the expression of XKS and TAL.

Data from growth analysis of the strains that were transformed with TAL and XKS genes in addition to the XI and Lyt-1 ORFs (variant C6, B9, A6, or C3) demonstrate that all of the triply transformed strains show extensive growth aerobically and anaerobically on CM glucose URA/TRP/LEU selective plates. These strains also show growth aerobically on CM xylose URA/TRP/LEU selective plates. None of the triply transformed strains grow anaerobically on CM xylose URA/TRP/LEU selective plates. Only the strains expressing C3 and XKS (not shown) or C6 and XKS show growth aerobically in CM xylose URA/TRP/LEU selective liquid medium. The triply transformed strains expressing B9 and XKS or A6 and XKS as well as all of the triply transformed strains expressing TAL do not grow in CM xylose URA/TRP/LEU selective liquid medium.

The triply transformed yeast strains, pSUMOduo/URA/HisXI-pSUMOduo/TRP/Lyt-1 (variant CS, B9, A6, or C3)-pSUMOduo/LEU/XKS-INVSc1, were analyzed using scanning electron microscopy (SEM) to determine morphology. Cells of the triply transformed yeast strain expressing XI, XKS and Lyt-1 variant C3 have large amounts of material on the outside of the cell in well-defined mats. Cells from the triply transformed yeast strain expressing XI, XKS, and variant C6 have no matted material on the outside, but a network of small tube-like structures is visible. The yeast strains expressing XI, XKS, and variants A6 or B9 show no mats and only a few tube-like structures. Scanning electron micrographs of the triply transformed cells grown aerobically in CM glucose URA/TRP/LEU selective liquid medium for about 2 days had ridges, dents, and bumps, but they were not as misshapen as those grown for 6 days in xylose. The triply transformed strain expressing XI, XKS, and variant C3 grown in glucose also had mats on the surface, but they were not as well-developed as the mats seen on that strain grown in xylose.

Lycotoxin-1 Mutants Affecting Xylose Utilization:

The amino acid changes from the wild-type sequence in the lycotoxin-1 variants C3 and C6 that favorably affected xylose utilization and the possible effects of these changes on the membrane permeabilizing function of the amphipathic peptide were examined. Mutations in positions 24 and 25 from lysine and leucine to proline and tryptophan, respectively, were present in both clone #59 (variant C3) and variant C6. In addition, variant C6 contained a mutation at position 9 from leucine to serine. The scanning electron micrographs suggest that in the case of the triply transformed strain expressing XI, XKS, and C3, considerable expressed protein appears on the outside of the cells, and that in the case of the triply transformed strain expressing XI, XKS, and C6, most of the material appears to be on the inside of the cells with a network of tube-like structures visible on the surface. An analysis of the material on the surface compared to the material in the cell lysate after cells were grown for 4 days in CM xylose URA/TRP/LEU selective liquid medium may be seen in the Coomassie gel. Cells expressing C3, which have matted material on the outside of the cells in the SEM images, show the presence of Lyt-1 on the outside of the cells, but essentially none is seen in the ethanol washings of the cells expressing C6. Cell lysates of both C3 and C6 show approximately the same amount of Lyt-1 in the cells overall.

Discussion

Three-Plasmid Yeast Expression Strategy:

The small ubiquitin-like modifier (SUMO) modulates protein structure and function by covalently binding to the lysine side chains of the target proteins. The structure of SUMO (also called Smt3) in aqueous solution consists of two α-helices and one β-sheet with 1 parallel and 3 antiparallel β-strands. Helix α1 (Leu45 to Gln56) is strongly amphipathic with hydrophobic residues pointing inward and hydrophilic residues directed toward the solvent (Sheng and Liao, 2002). Attachment of SUMO to the N-terminus of proteins has been found to enhance their expression (Malakhov et al., 2004). Yeast cells contain a protease (Ulp1 or SUMO protease 1) that can cleave a variety of SUMO fusions (Li and Hochstrasser, 2003). The enhanced expression and solubility of proteins or peptides fused to SUMO combined with the broad specificity and highly efficient cleavage properties of SUMO protease make this a useful system for obtaining high levels of expression of functional proteins (Malakhov et al., 2004). Plasmid 1 of the 3-vector SUMO system was used to express the PCR-assembled xylose isomerase ORF. Here the full XI ORF was assembled to ensure that rapid high-level expression of properly folded XI was obtained. Misfolding has been identified as an issue in the functional expression of XI for efficient ethanolic fermentation of xylose (Kuyper et al., 2003). The SUMO protease 1 in yeast is highly efficient and cleaves the SUMO tag to completion giving large amounts of functional enzyme (Malakhov et al., 2004). Plasmid 2 was used for expression of the lycotoxin-1 clone library produced by amino acid scanning mutagenesis to allow automated high-throughput plasmid production and expression of this test peptide. Alternatively, the second vector can be used to introduce other mutagenized open reading frames such as cellulases (Den Haan et al., 2007) to produce improved yeast strains for industrial use in conjunction with the XI gene to enable xylose utilization. Plasmid 3 makes possible the introduction of additional clones of interest. These could be obtained from traditionally produced cDNA libraries using Superscript reverse transcriptase or from the FLEXGene collections (Zuo et al., 2007) of expression-ready fully annotated inserts for full-genome library introductions or ordered grid transformations of select FLEXGene sets. This plasmid allows expression of enzymes for corrective metabolic pathways or other desirable functions to improve tolerance, anaerobic growth, and increase ethanol output in industrial yeast strains. High levels of expression are obtained from all three plasmids.

Expression of Xylose Isomerase:

The transmission electron micrograph (TEM) of the INVSc1-XI yeast strain compared to that of the INVSc1 yeast strain shows the XI-yeast contains large amounts of additional material not seen in the strain without the XI plasmid. Although the cells change dramatically in shape, growth does not appear to be adversely affected since the doubling time on glucose is the same for both the INVSc1 yeast strain and the INVSc1-XI yeast strain (1.8 hours). The presence of expressed XI enzyme is verified by the appearance of the 53.7 kD attB1HisXI band on the Western gel. Expression of xylose isomerase enables the XI-strain to grow aerobically on CM xylose URA selective plates to a very limited extent. This strain has potential for use in the metabolic engineering of a pentose-fermenting industrial *S. cerevisiae* strain for production of bioethanol from renewable lignocellulosic feedstocks (Hahn-Hägerdal et al., 2007; Kuyper at al., 2003).

Expression of Lycotoxin-1 Mutants:

The function of lytic peptides such as lycotoxin-1 is to destroy target cells by disrupting the cell membrane and causing cell lysis. Common features of these peptides include an overall basic charge, a small size (23-39 aa residues), and the ability to form amphipathic α-helices. Whether they function by disruption of the membrane lipid bilayer via the amphipathic α-helix portion or by ion channel formation, an ordered secondary conformation such as an amphipathic α-helix and a positive charge appear to participate in the lytic function (Corzo et al., 2002; Duguid et al., 1998; Julian et al., 1998; Kourie and Shorthouse, 2000). The net positive charge promotes interaction with negatively charged prokaryotic membranes (mammalian cells have more positive-charge character) Both composition and sequence contribute to function (Mayo et al., 2000). Expression of the lycotoxin-1 variants does not appear to disrupt the yeast cells since the doubling time of the lycotoxin-containing yeast cultures on glucose (1.9 hours) is the same as that for the INVSc1 and INVSc1-XI-yeast strains. Using the Penta-His antibody Alexa Fluor staining protocol, fluorescence images of the INVSc1 strain show no signal, indicating absence of expression of any His-tagged species, while the INVSc1-XI strain shows extensive and intense staining of the large amount of HisXI and HisSUMO throughout the cells but most strongly in areas with the obvious dent visible in the brightfield images, consistent with expression of XI. In spite of high levels of expression of XI and the presence of indentations, the cells show normal growth on glucose. The INVSc1-XI-Lyt-1 strains show more intense and widespread staining than the INVSc1-XI strain, also around the indentations, from expression of HisLyt-1 and more HisSUMO in addition to the HisXI and HisSUMO from plasmid 1. Both Lyt-1 and SUMO are amphipathic peptides. Localization of an amphipathic peptide is strongly dependent on the charge and hydrophobic nature of the peptide and the charge on the cell membranes (Parenteau et al., 2005; Holm et al., 2005). Immunofluorescence shows that large quantities of His-tagged material are present in the INVSc1-XI and INVSc1-XI-Lyt-1 yeast strains after 2-day growth, both processed and undergoing further processing. SUMO undergoing processing is known to localize to the nucleus (Stade et al., 2002; Li and Hochstrasser, 2003), but it is not clear in exactly which structures the material is localized. The Western gels suggest that the Lyt-1 is associated with the membrane and remains associated with membrane components in the lysate. When the His-tagged Lyt-1 is Ni bead purified, the Lyt-1 molecules are pulled away from the membrane components and bound to the beads. Their close proximity provides the opportunity for aggregation, with dimers seemingly favored. The SEM and Coomassie gel results suggest that more of the expressed Lyt-1 is inside the yeast cells rather than on the surface in the C6 and A6 variant strains compared to the C3 variant strain.

Expression of Xylulokinase or Transaidolase Genes:

Lysates prepared after growth on glucose of all 12 yeast strains expressing xylose isomerase and the lycotoxin-1 variants, either with or without one of two pentose phosphate pathway enzymes, show the expected bands for attB1HisXI, the attB1HisEntKLyt-1, and the HisSUMO tag removed from both HisXI and HisLyt-1 by yeast SUMO protease 1. The band for the HisSUMO tag is twice as intense as either of the other two bands since it is released from both the XI protein and the lycotoxin-1 variants. Lysates prepared after growth on glucose and subjected to Ni bead purification of the His-tagged proteins, show bands at the same 3 locations (with a decrease in intensity of the 10.7 kD attB1HisEntKLyt-1 band) and an additional band at 21.4 kD, attributed to a dimer of the attB1HisEntKLyt-1 protein for all 12 strains. Diner formation is postulated because in the Ni bead purification the beads concentrate the peptide on their surface and highly favor aggregation. Amphipathic peptides tend to aggregate (Kourie and Shorthouse, 2000). As would be expected, the monomer band is dramatically decreased in intensity since it is being used to form dimer. Aggregation most probably contributes to the invaginations, tube-like formations and matted material seen in the scanning electron micrographs. The pore-forming properties of the amphipathic peptides might allow the cells to accommodate the large amount of expressed protein produced in the triply transformed yeast cells.

Growth of Triply Transformed INVSc1 Yeast Strain:

The INVSc1-XI-Lyt-1 (C3, A6, B9, or C6)-XKS (or TAL) strains grow better aerobically, although still to a limited extent, on CM xylose plates than INVSc1-XI, with the XKS strains showing slightly better growth than the TAL strains. The triply transformed strains show extensive growth aerobically and anaerobically on CM glucose liquid medium and on CM glucose plates. Interestingly, the strains expressing XKS and C or XKS and C3 show growth aerobically on CM xylose URA/TRP/LEU selective liquid medium. This would suggest that overexpression of an enzyme that contributes to xylose utilization via the pentose phosphate pathway may help to correct metabolic imbalance caused by overexpression of xylose isomerase. The process stalls because the next enzyme in the pathway is not available in sufficient quantity. Growth is not yet at an industrial level, but this work demonstrates that the SUMO 3-plasmid system can be used to express high levels of several proteins that enhance xylose utilization simultaneously. The INVSc1-XI-XKS strain showed optimum growth on xylose liquid medium with a doubling time of 5.87 hours. Previous work in another laboratory showed a doubling time on xylose of about 8 hours (Van Maris et al., 2007). The INVSc1-XI-XKS strain developed in the work described here will be used as the base strain for further development by addition of genes from a full-genome yeast library and from other xylose-utilizing fungi and yeast.

Effects of Lycotoxin-1 Mutations:

The 4 mutants used in this work were the most effective in killing a test insect pest (Hughes et al., 2007 and 2008). They all have proline and tryptophan replacing lysine and leucine at positions 24 and 25, respectively. Tryptophan is important to activity of amphipathic peptides (Blondelle et al., 1993; Salzwedel, et al., 1999). The variant, C6, in the INVSc1-XI-XKS strain that showed limited growth aerobically in xylose liquid medium also had the substitution of serine for leucine at position 9. These lycotoxin-1 variants still retain the core set of lysine residues, K7, K1, K15, and KL9, present on the hydrophilic side of the α-helix in the amphipathic peptide structure, giving the net positive charge that promotes interaction with the negatively charged surface of the target cell membranes. The mutation of lysine to proline at position 24 increases the hydrophobic nature of the hydrophobic side of the α-helix, which promotes cell membrane permeabilization. It also places a hydrophobic residue at the C-terminal position, which appears to be important for greatest activity (Mayo et al., 2000). The function of amphipathic peptides such as lycotoxin-1 is the modification of cell membranes, making them more permeable. Several models have been proposed for pore or channel formation (Kourie and Shorthouse, 2000). In one model proposed for the frog toxin magainin the molecules are arranged in dimers of α-helices aligned to form antiparallel amphipathic units with hydrophobic side outward into the lipid membrane and hydrophilic side inward into the pore. Similarly, a possible model for lycotoxin-1 includes the hydrophobic residues including the tryptophans directed toward the interior of the cell membrane and the hydrophobic residues forming the interior of the pore. Xylose uptake by the cells is dependent on hexose-transporter genes. Deletion of all the hexose transporter genes results in loss of the ability to grow on xylose (Hamacher et al., 2002). It is possible that the presence of a pore-forming amphipathic peptide increases transport of xylose into the cells by increasing surface area to allow greater transporter activity.

In summary, the yeast strains expressing xylulokinase in addition to xylose isomerase show improved aerobic growth on xylose liquid medium compared to the XI-yeast. Strains expressing lycotoxin-1 variants C6 and C3 in addition to XI and XKS also show limited aerobic growth on xylose liquid medium. The three-plasmid system provides a strategy for introducing genes for further improvements.

EXAMPLE 3

Engineering the industrial ethanologen *Saccharomyces cerevisiae* to ferment pentose sugars from lignocellulosic biomass is critical for commercializing cellulosic fuel ethanol production. Expression of xylose isomerase, from the anaerobic fungus *Piromyces* confers the ability to ferment xylose, but fermentation rates are slow. A high throughput strategy was implemented to improve fermentation rate by evaluating over-expression of each native *S. cerevisiae* gene: a haploid PJ69-4 MATa XI-expressing strain was mated with haploid PJ69-4 MATa strains containing the *S. cerevisiae* expression library of genes driven by an ADH promoter. The resulting 6113 mated diploid strains containing the XI ORF and a different yeast library clone were screened for growth on xylose in anaerobic solid cultures using an integrated robotic workcell. Nine strains were recovered from the screen, but two were eliminated when it was discovered they had lost the ability to grow on glucose. The seven strains were further evaluated for fermentation of wheat straw alkaline hydrolysate and all seven successfully utilized glucose and xylose. Additional expression of xylulokinase (XKS), introduced with the pSUMOduo RGStetHis-tagged gene, did not further improve anaerobic growth on xylose but did improve ethanol production on the hydrolysate.

Materials and Methods

Strains:

Two haploid *S. cerevisiae* strains were used (Drees et al., 2001). They are identical except for mating type:

PJ69-4 MATa: MATa, trp1-901, leu2-3, ura3-52, his3-200, gal4Δ, gal80Δ, GAL2-ADE2, LYS::GAL1-HIS3, met2::GAL7-lacZ PJ69-4MATalpha: MATalpha, trp1-90, leu2-3, ura3-52, his3-200, gal4Δ, gal80Δ, GAL2-ADE2, LYS::GAL1-HIS3, met2::GAL7-lacZ Production of pDEST32-XI Trp Selectable Haploid PJ69-4 MATalpha Strain:

The pDEST32-XI TRP selectable plasmid was constructed by replacing the LEU2 gene in the pDEST32 LEU2 selectable bait plasmid commercially available in the ProQuest Two-Hybrid System kit (Invitrogen, Carlsbad, Calif.) with the TRP1 gene. The TRP1 marker was PCR amplified from pRS404 using the forward primer, leu2::TRP1 (S): 5' CATTTCAG-CAATATATATATATATATTTCAAG-GATATACCATTCTAATGTCTGTTATTAATT TCA-CAGGT3' (Sequence ID No. 26) and the reverse primer, leu2::TRP (AS): 5' TTTCATTTATAAAGTTTATGTA-CAAATATCATAAAAAAAGAGAATCTTTC-TATTTCTTAGCA TTTTTGA (Sequence ID No. 27) to generate 40 nucleotides of flanking homology to the 5' and 3' ends of the LEU2 open reading frame fused to the TRP1 marker [5'leu2::TRP1:3'leu2 fragment]. Yeast cells (InvSc1) were transformed with 500 ng of the 5'leu2::TRP1::3'leu2 fragment and 25 ng of linearized pDEST32 with LEU marker using a standard lithium acetate procedure. Trp+ Leu− isolates were identified and the plasmid from these strains was rescued into *E. coli*. This pDEST32 plasmid has the LEU2 marker deleted and replaced with the TRP marker. Plasmid preparation was performed and the plasmid rescued into the PJ69-4 MATalpha haploid yeast strain. The *Piromyces* xylose isomerase (XI) open reading frame was cloned into the resulting TRP selectable modified bait plasmid using standard Gateway recombination procedures with LR clonase, as described previously (Hughes et al., 2005). The XI ORF was obtained using forward primer 5'ATGGCTAAG-GAATATTTCCCAC3' (Sequence ID No. 28) and reverse primer 5'-CGAAGCTATTGTTGCCATGTACCAATAA3' (Sequence ID No. 29) to amplify the XI coding region from the pENTR D TOPO XI vector constructed previously (Hughes et al., 2008). The amplified fragment was isolated using GENECLEAN II PCR kit (MP Biomedicals, Solon, Ohio) according to the manufacturer's directions and recombined into the pDEST 32-TRP vector using LR clonase II (Invitrogen). The resulting ligations were transformed into TOP10 competent cells (Invitrogen) according to manufacture's instructions and grown overnight at 37° C. Colonies were picked into 1.6 mL LB AMP 50 medium (Teknova). Plasmids were isolated from the cultures using Qiagen plasmid preparation kit. The resulting yeast expression plasmid pDEST32-XI TRP selectable was verified by sequencing and transformed into PJ69-4MATalpha using EZ yeast clone procedures. Yeast cells (3-4 mm size colonies) were inoculated into YPD+ADE (Teknova) (25 mL) using a sterile loop and incubated for 2 days at 30° C. with shaking at 150 rpm. One mL of culture was pelleted at 1300 rpm in a microfuge (Thermo Electron) and 125 μL of EZTransformation solution, 2 μg of plasmid DNA, and 5 μL carrier DNA were added. The cells were resuspended by vortexing at moderate speed for 1 min, incubated at 30° C. for 30 min, and transferred to CM glucose TRP selective medium plates, spread with a sterile spreader, and incubated at 30° C. until transformants were observed (typically 3 days).

Production of Haploid PJ69-4 MATa Strain Containing Library of pOAD Plasmids with Yeast Full-Genome Clones:

Yeast full-genome library clones in pOAD LEU selectable plasmids transformed into PJ69-4 MATa haploid yeast strain and spotted in a 384-grid pattern on sixteen 86×128 mm Omnitrays containing CM glucose −LEU+ADE medium were provided by Dr. Stanley Fields at University of Washington, Seattle, Wash. (Uetz et al., 2000; Phizicky et al., 2003).

Automated mating of PJ69-4 MATalpha haploid strain containing pDEST32-XI TRP selectable vector to a PJ69-4 MATa haploid strain containing *S. cerevisiae* library of full-length clones in a pOAD LEU selectable vector:

The 384-grid colony plate containing the PJ69-4 MATa haploid strain with the *S. cerevisiae* library of full-length clones in the pOAD LEU selectable vector was placed on the liquid handler deck and used to inoculate 50 μL CM 2.0% glucose-LEU+ADE liquid medium (Teknova) in sixteen 86×128 mm Omnitray agar plates (VWR) with 384×5 μL spot colonies representing the yeast library for 2-day culture. A 384-well Matrix deepwell plate (Fisher) containing 50 μL CM glucose −LEU+ADE medium is inoculated with the library of pOAD clones in haploid PJ69-4 MATa yeast strains and grown for 2 days at 30° C. The plate is sealed and brought to the liquid handler for mating with the PJ69-4 MATalpha strain containing pDEST32-XI TRP selectable vector to produce diploid PJ69-4 yeast strains each containing two plasmids.

A sterile trough containing 150 mL of PJ69-4 MATalpha haploid yeast with pDEST32-XI TRP selectable vector in CM glucose −TRP+ADE (Teknova) grown for 2 days at 30° C. is placed onto the liquid handler deck. Mating is performed in a Matrix 384-well deepwell plate containing 50 μL of YPD+ ADE (Teknova) seeded with 30 μL of PJ69-4 MATa cultures with pOAD yeast clone LEU selectable plasmids and 20 μL of MATalpha PJ69-4 yeast strain with pDEST32-XI TRP selectable plasmid. Cultures are grown for 1 day at 30° C. in YPD+ADE medium.

Sealed Matrix 384-well deepwell 1-day culture plates containing mated diploid PJ694 strains with pOAD yeast clone plasmids and pDEST32-XI plasmid are pierced by the sterile stainless steel pipet tips of the liquid handler, and 20 mL are diluted in a new 384-well deepwell plate containing 100 μL CM glucose −LEU−TRP+ADE liquid medium and grown for 10 hours at 30° C. The 384-well deepwell dilution cultures in CM glucose −LEU−TRP+ADE medium are broadcast from the 384-well format into 4×96-well ABgene pyramid bottom deepwell plates containing the same medium, and grown at 30° C. for 2 days.

Sealed ABgene 96-well deepwell cultures containing the diploid PJ694 yeast strain with pDEST32-XI TRP selectable plasmid and pOAD LEU selectable plasmids with the yeast library clones were pierced by the sterile stainless steel pipet tips of the liquid handler, and 20 μL are diluted in a new 384-well deepwell plate containing 100 μL CM glucose −LEU−TRP+ADE liquid medium. Three μL of the dilution cultures are spotted in 96-well format onto CM xylose −LEU−TRP+ADE medium on 86×128 mm Omintray agar plates and incubated in a fully anaerobic chamber (Becton Dickinson) for 6 days at 30° C.

Colonies that grew out after 6 days in an anaerobic chamber were picked into CM glucose −TRP−LEU+ADE medium to make glycerol stock. Two of the 10 strains did not grow out on glucose; the remaining 8 were re-plated onto CM xylose −LEU−TRP+ADE plates grown anaerobically again, and these colonies were selected for growth and ethanol productivity analysis.

Construction of RGStetHis-XKS Plasmid and Production of Triple-Plasmid Diploid Strain:

The RGStetHis-tagged XKS plasmid was constructed by using the forward XKS primer with RGSHHHH tag, Oligo 1 (88-mer; GC content: 46/88), BBCHTS 7-2-08A:

(Sequence ID No. 30)

5' CACCATGAGAGGTTCTCATCACCATCACCCAACTTTGTACAAAAAAG

CAGGCTCCGCGGCCGCCCCCTTCACCATGTATGTTGGTATC3' and reverse XKS primer, Oligo 2 (27-mer; GC content: 12/27), BBCHTS 7-2-08B:

(Sequence ID No. 31)

5' CTACTCACACAATGGCAGCAATTGTTG3' to add the RGStetHis tag to the XKS sequence in the pENTR D TOPO XKS plasmid. The RGStetHis-XKS gene was then Gateway cloned into the pSUMOduo TRP selectable vector. The resulting vector was used to transform TOPIC competent cells, and plasmids were produced as described previously (Hughes et al., 2005). The resulting pSUMOduo-RGStetHis-XKS TRP selectable plasmid was transformed into the double-plasmid diploid strains to give the triple-plasmid diploid strains.

Anaerobic Growth of Multiplasmid Strains on Single Sugars (Glucose or Xylose):

Plates from the liquid handler containing multiplasmid diploid yeast strains were placed in an incubator (Becton Dickinson) at 30° C. with anaerobic conditions maintained using BD GasPak EZ Gas Generating Container Systems with Indicator (Becton Dickinson, Franklin Lakes, N.J.). For growth on glucose, samples were streaked on CM glucose selective plates. For growth on xylose, similar plates were used but CM xylose was substituted for CM glucose. For anaerobic growth the plates were first placed in an anaerobic chamber for at least 2 hours and then samples were applied. The plates were wrapped and placed back into the anaerobic chamber for 6 days.

Analysis of Ethanol from Single Sugar (Glucose and Xylose) Anaerobic Cultures:

Plate cultures were analyzed in triplicate for ethanol productivity using gas chromatography (6890N; AgilentTechnologies, Wilmington, Del.) with a packed column as described previously (Qureshi et al., 2007). Before injection into the GC, the sarples were diluted 4-fold with distilled water. The GC was equipped with an autosampler and an integrator. Ethanol productivity was calculated as g $L^{-}$. Plate cultures were analyzed in triplicate for xylose and glucose concentrations using Surveyor HPLC equipped with an automatic sampler/injector (Thermo Electron Corporation, West Palm Beach, Fla.). The HPLC column (Aminex HPX-87P; Resin based) was obtained from BioRad (Hercules, Calif.). Solvent (MilliQ water) flow rate was maintained at 0.6 mL $min^{-1}$. For sugar analysis, the mixture was centrifuged at 15,000X·g for 15 min followed by 20-fold dilution and injection into the HPLC (Qureshi et al., 2007).

Wheat Straw Hydrolysate Production:

Wheat straw was purchased from a local farmer, dried in a forced-air oven at 55° C. for 24 hours, and milled in a hammer mill to pass through a 1.27 mm screen. Milled wheat straw was slurried in water (8.6%, w/v) containing $H_2O_2$ (0-4.3%, v/v), adjusted to pH 11.5 using NaOH, and shaken in an incubator at 250 rpm at 25 or 35° C. for 3-24 hours. The pretreated wheat straw was adjusted to pH 5.0 using concentrated HCl before enzymatic saccharification (Saha and Cotta, 2006). Enzymatic saccharification was performed by shaking gently (100 rpm) at 45° C. and adding enzymes at each enzyme dose of 4 mL/100 g of wheat straw for 72 to 120 hours (Saha and Cotta, 2006) Carboxymethyl cellulase (CMCase) and xylanase activities were assayed in a reaction mixture (0.5 mL) containing 1% (w/v) carboxymethyl cellulose and 1% (w/v) oat spelt xylan, respectively, 50 mM acetate buffer, pH 5.0, and appropriately diluted enzyme solutions. After 30 min incubation at 50° C., the reducing sugar liberated in the reaction mixture was measured by the dinitrosalicylic acid (DNS) method (Miller, 1959). One unit (U) of each enzyme activity is defined as the amount of enzyme that produces 1 μmol of reducing sugar as glucose (xylose in the case of xylanase) per minute. α-Glucosidase, α-xylosidase, and R-L-arabinofuranosidase activities were assayed in the reaction mixture (1 mL) containing 4 mM p-nitrophenyl-α-D-glucoside, 2 mM p-nitrophenyl-α-D-xyloside, or 1 mM p-nitrophenyl-R-L-arabinofuranoside, respectively, 50 mM acetate buffer, pH 5.0, and appropriately diluted enzyme solutions. After incubation at 50° C. for 30 min, the reaction was stopped by adding 1 mL ice-cold 0.5 M $Na_2$ $CO_3$, and the color developed from p-nitrophenol liberation was measured at 405 nm (Saha and Cotta, 2006). One unit (U) of each enzyme activity is defined as the amount of enzyme that produces 1 μmol of p-nitrophenol per minute in the reaction mixture.

Analysis of Hydrolysates for Cell Growth and Concentrations of Glucose and Xylose:

Samples (1 mL) were withdrawn with an 18-gauge needle from 25 mL cultures in a 50 mL Erlenmeyer flask after 5- and 8-days growth in the hydrolysate at 3° C. with shaking at 100 rpm. The flask was closed with a rubber stopper and covered with porous tape to maintain sterility. Glucose, xylose, and ethanol were analyzed by high-pressure liquid chromatography (HPLC) (Saha and Cotta, 2006)). The separation system consisted of a solvent delivery system (P2000 pump, Spectra- Physics, SanJose, Calif.) equipped with an autosampler (717, Waters Chromatography Division, Millipore Corp., Milford, Mass.), a refractive index detector (410 differential refractometer, Waters), a dual λ absorbance detector (2487, Waters), and a computer software based integration system (Chromruest 4.0, Spectra-Physics). Two ion moderated partition chromatography columns (Aminex HPX-87P with De-ashing and Carbo-P micro-guard cartridges; Aminex HPX 87H with Cation H micro-guard cartridge; Bio-Rad Laboratories, Inc., Hercules, Calif.) were used. The HPX-87P column was maintained at 85° C., and the sugars were eluted with Milli-Q filtered water at a flow rate of 0.6 mL/min. The HPX-87H column was maintained at 65° C., and the sugars and ethanol were eluted with 10 mM $HNO_3$, prepared using Milli-Q filtered water at a flow rate of 0.6 mL/min. Peaks were detected by refractive index or UV absorption (277 nm) and were identified and quantified by comparison to retention times of authentic standards. Cell growth of the yeast strains was monitored by measuring the optical density of the appropriately diluted culture sample at 660 nm.

Results and Discussion

Production and Isolation of Anaerobic Multiplasmid Diploid Yeast Strains:

The yeast mating protocol that was successfully developed for production and screening of multiplasmid diploid yeast strains described above is also summarized in a schematic diagram in Hughes (2009, JALA, 14:190-199). This method was used to mate an a type haploid expressing XI to a *Saccharomyces* genome over-expression library hosted in an alpha type haploid. Using this method, ten diploid *S. cerevisiae* PJ69-4 yeast strains were isolated that grew anaerobically on xylose selective medium. In Example 1 *S. cerevisiae* INVSc1 strains capable of only aerobic growth on xylose were isolated. The selected strains were analyzed and found to contain the yeast genome full-length clones, designated PIP2, IMG2, MAK5, VPS9, COX10, ALE1, CDC7, MMS4, -G1, and -G2, in the pOAD TRP selectable plasmid. The first 8 of these retained the ability to grow anaerobically on glucose. In addition to the plasmid containing one of the clones, the two-plasmid diploid PJ69-4 yeast strains contained the *Piromyces* sp. XI ORF in the pDEST32 LEU selectable plasmid. The three-plasmid diploid PJ69-4 yeast strains were additionally transformed with the pSUMOduo-RGStetHis-XKS URA selectable plasmid. The entire production and screening process was carried out on the integrated robotic platform described previously (Hughes et al., 2005 and 2006). The two-plasmid and three-plasmid strains that grew anaerobically on xylose and glucose were analyzed for growth rate and ethanol production to identify the strains that demonstrated optimum anaerobic growth on xylose and glucose combined with high ethanol productivity from wheat straw alkaline hydrolysate.

Growth of Multiplasmid Diploid PJ69-4 Yeast Strains:

Doubling times for anaerobic growth on glucose and xylose of *S. cerevisiae* double-plasmid and triple-plasmid diploid strains derived from mating of PJ69-4 MATalpha strain expressing *Piromyces* XI with PJ69-4 MATa strain expressing one of the yeast library clones and transformation of those strains with pSUMOduo RGStetHisXKS URA selectable plasmid are presented in Table 6. The double-plasmid strains expressing clones PIP2 and IMG2 demonstrated the shortest doubling times on glucose medium. Similarly, the shortest doubling times on glucose medium for the triple-plasmid strains included the strain expressing clone MMS4 as well as those expressing clones PIP2 and IMG2. The double- and triple-plasmid strains expressing clone IMG2 also were in the top 2 shortest doubling times grown on xylose along with the double- and triple-plasmid strains expressing clone MAK5. The double- and triple-plasmid strains expressing clone PIP2 had much longer doubling times when grown on xylose than the strains expressing clones IMG2 or MAK5.

Growth curves of the two-plasmid diploid strain (Clone-XI) cultures with and without expression of XKS grown anaerobically on glucose (FIGS. 1 A & B) and xylose (FIGS. 1 C & D) indicate, as expected, that all the strains grow more slowly on xylose than glucose. It is also clear from comparing the double-plasmid curves to the triple-plasmid curves on either glucose or xylose medium that addition of XKS did not improve growth rate.

Figure 2:
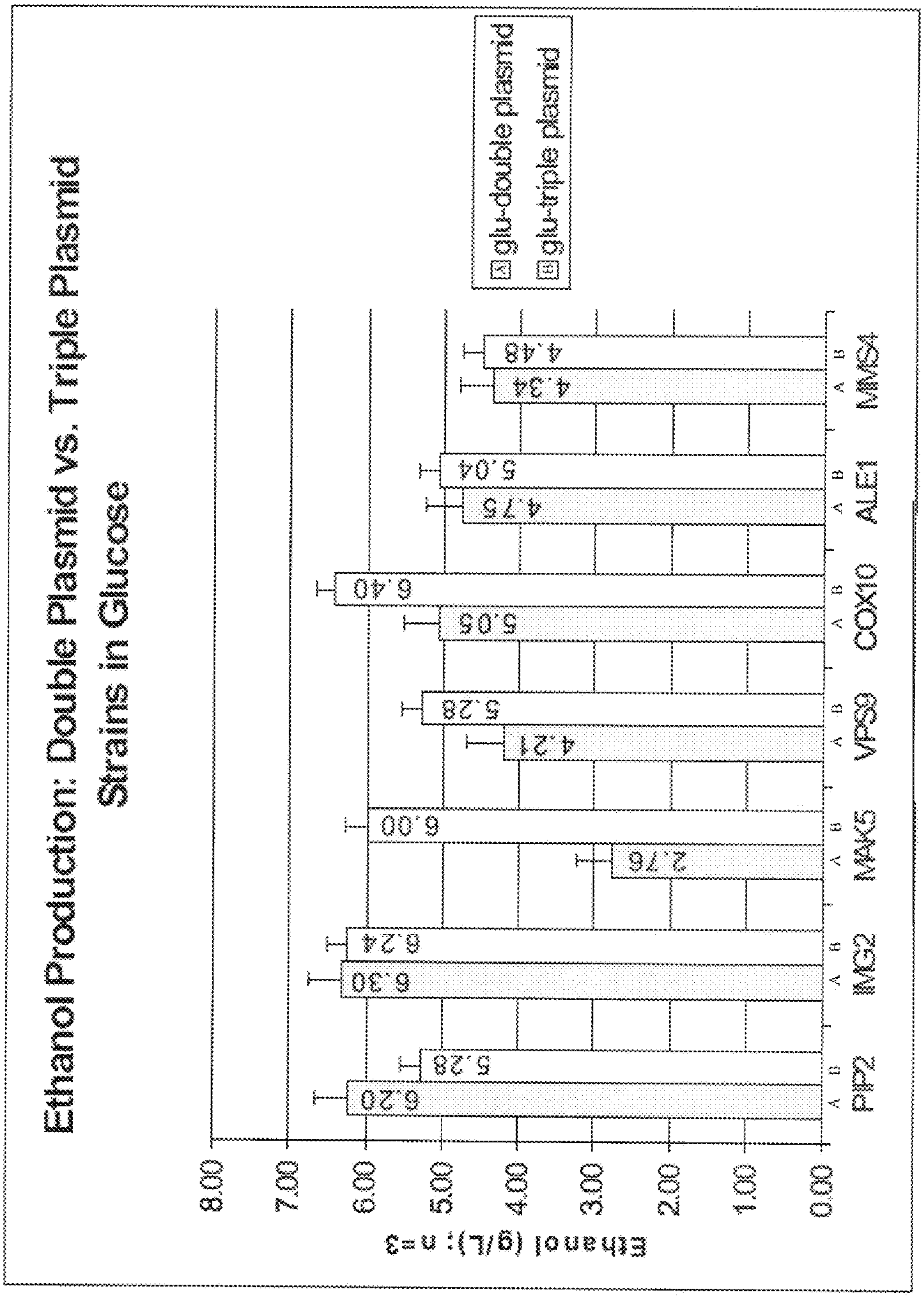
FIG. 2 shows the ethanol production from double-plasmid and triple-plasmid strains on glucose selective medium in Example 3. No ethanol was seen from the double-plasmid or triple-plasmid transformed strains grown on xylose selective medium.

Ethanol Productivity of Multiplasmid Diploid PJ69-4 Yeast Strains Grown on Glucose:

Diagram of ethanol from double-plasmid and triple-plasmid strains on glucose selective medium shows that overall more ethanol is produced from those strains having the XKS gene expressed (FIG. 2). No ethanol was seen from the double-plasmid or triple-plasmid strains grown on xylose alone. The double-plasmid and triple-plasmid strains expressing clones PIP2 and IMG2 gave the highest ethanol productivity on glucose.

Ethanol Production, Glucose and Xylose Usage, and Optical Density of Multiplasmid Diploid PJ69-4 Yeast Strains Grown on Wheat Straw Alkaline Hydrolysate:

Maximum amounts of ethanol produced after 100 hours reaction from double-plasmid (XI-PIP2) and triple-plasmid (XI-Clones PIP2, IMG2, MAK5, VPS9, or MMS4-XKS) diploid PJ69-4 yeast strains that gave optimum growth on alkaline hydrolysate are shown in FIG. 3, in addition to the xylose and glucose levels and optical density at 600 nm. When grown on wheat straw alkaline hydrolysate, the highest ethanol production, best glucose and xylose usage, and greatest optical density occurred in triple-plasmid strains expressing clones PIP2, IMG2, and MMS4. The triple-plasmid strains expressing clones MAK5 and VPS9 gave almost as much xylose and glucose use and ethanol production; however, the optical density was dramatically lower. The reason for this result is not clear. On wheat straw alkaline hydrolysate, all seven strains first utilized glucose with production of ethanol, followed by slower consumption of xylose accompanied by further ethanol production from the remainder of the glucose.

Description of Clones:

Sequence identification and function of seven unique clones that allow completely anaerobic growth on xylose, including *Saccharomyces* Genome Database (SGD) nomenclature and maximum ethanol production for triple-plasmid *S. cerevisiae* strains derived from mating of the PJ69-4 MATalpha bait strain expressing *Piromyces* XI attached to the binding domain (BD) of GAL4 with a PJ69-4 MATa strain expressing one of the yeast full-genome library clones attached to the GAL 4 activation domain (AD) and transformation with pSUMOduo RGStetHisXKS URA selectable plasmid is presented in Table 6. Those triple-plasmid strains expressing clones PIP2, IMG2, and MMS4 gave the highest ethanol productivity at 14.0 g/L, 14.3 g/L and 14.12 g/L, respectively.

CONCLUSION

Nine unique full-length yeast genomic library clones were identified that allowed growth on xylose plates in a completely anaerobic chamber of the double-plasmid diploid *S. cerevisiae* strains expressing the clone and xylose isomerase (XI). Seven of these strains were still able to grow anaerobically in glucose liquid culture. Additionally it was found that transforming the double-plasmid strains with a plasmid expressing xylulokinase (XKS) did not aid anaerobic growth of these XI-library clone strains on xylose. No ethanol production occurred on xylose. The double-plasmid and triple-plasmid strains expressing clones PIP2 and IMG2 gave the highest ethanol productivity on glucose. When grown on wheat straw alkaline hydrolysate, the highest ethanol production, best glucose and xylose usage, and greatest optical density occurred in triple-plasmid strains expressing clones PIP2, IMG2, and MMS4. The triple-plasmid strains expressing clones MAK5 and VPS9 gave almost as much xylose and glucose use and ethanol production; however, the optical density was dramatically lower. On wheat straw alkaline hydrolysate, all seven strains first utilized glucose with production of ethanol, followed by slower consumption of xylose accompanied by further ethanol production from the remainder of the glucose.

It is understood that the foregoing detailed description is given merely by way of illustration and that modifications and variations may be made therein without departing from the spirit and scope of the invention.

TABLE 1

Comparison of xylose isomerase (XI) produced in yeast strain containing single copy chromosomal expression cassette with and without SUMO. The data is obtained from densitometry analysis of western blot using Multi Gauge 3.0 software (Fujifilm Life Science). Density was calculated by measuring absorbance units (AU) by the image analyzer and by subtracting background and dividing by area. Comparison was made between the protein levels obtained from strains expressing His-XI and His-SUMO-XI.

| Yeast Strain | Relative intensity of SUMO band (AU) | Relative intensity of XI band (AU) |
|---|---|---|
| His-XI expression cassette | 115 | 139 |
| His-SUMO-His-XI Expression cassette | 1073 | 1350 |

TABLE 2

The oligonucleotides A to R used in the gene assembly protocol adapted for the automated robotic platform.
OLIGONUCLEOTIDES USED IN THE PROMYCES XYLOSE ISOMERASE GENE ASSEMBLY STRATEGY

| OLIGO | DESCRIPTION | USDA NUMBER | SEQUENCE |
|---|---|---|---|
| A | Short forward primer for all sections | FBTHTS 6-20-04C OLIGO | 5-CACCATGCATCATCATCATCATCATATGGC-3 |
| B | XI section 1 forward oligo | FBTHTS 6-20-04A OLIGO | 5-CACCATGCATCATATCATCATCATATGGCTAAGGAATAT TTCCCACAAATTCAAAAGATTAAGTTCGAAGGTAAGGATTC TAAGAATCCATTAGCCTTCCACTAC-3 |
| C | XI section 2 reverse oligo | FBTHTS 6-20-04B OLIGO | 5-TTAACCTTCGGCGCAAAGAGTGTGCCACCAGGCCATGGC GAAACGTAACCAATCCTTCATTTTCTTACCCATGACTTCCT TTTCAGCATCGTAGTAGTGGAAGGCTAATG-3 |
| D | XI section 3 long reverse oligo | FBTHTS 7-23-04A OLIGO | 5-CAACATCGTGGAAACAGTAGTATGGAATACCAAGCTTTT GCATGATTTCGAAACCAGCATCAACCTTTTGCTGGCAATTT CAATAGCATCAGTACCTTCGTTCCATGGG-3 |
| E | XI section 4 long reverse oligo | FBTHTS 8-20-04CD OLIGO | 5-AAGATCAACATCGTGGAAACAGTAGTATGGAATACCAAG CTTTTGCATGATTTCGAAACCAGCATCAACCTTTTGCTGGC AATTTCAATAGCATCAGTACCTTCGTTCC-3 |
| F | XI section 5 long reverse oligo | BBCHTS 2-17-05C OLIGO | 5-TCCTTTTGCTTTTCCTTGAGGTAAGCAACGACAGCCTTA AGGTTGGATCGTATTCTTCAATAGAGTTACCTTCGGAAACA AGATCAACATCGTGGAAACAGTAGTATGG-3 |
| G | XI section 6 long reverse oligo | BBCHTS 2-17-05D OLIGO | 5-CTGGGTTAGTGGAGGCACCGTTCATGTAACGCTTGTGAC CGAAGACGTTAGCAGTACTCCAGAGAAGCTTAATACCGGTT TCCTTTTGCTTTTCCTTGAGGTAAGCAACG-3 |
| H | XI section 7 long reverse oligo | BBCHTS 2-17-05E OLIGO | 5-GTTTTCAGCACCAAGTTCAATACCGGCGTCTATGGCGTT CTTAATTTGAACAATAGCACGGGCGACAACATCAAAGTCTG GGTTAGTGGAGGCACCGTTCATGTAACGC-3 |
| I | XI section 8 long reverse oligo | BBCHTS 2-17-05F OLIGO | 5-ATAGTGGCCATGTGTTCCTTTTCACGCTTTTGGTCAGTG TTAAGGAGACTCATGTAACCTTCACGACCACCCCAGAAGAC GTAGTTTTCAGCACCAAGTTCAATACCGGC-3 |
| J | XI section 9 long reverse oligo | BBCHTS 2-17-05G OLIGO | 5-TGGTTGGTTCCATTGGCTTTGGTTCAATGAGGAAAGTAC CCTTGAATCCCTTGGAACGAGCGTAGTCACGAGCCATGGTA AGCATAGTGGCCATGTGTTCCTTTTCACGC-3 |
| K | XI section 10 long reverse oligo | BBCHTS 2-17-05H OLIGO | 5-TGACCTTGAAGTCCTTGTCTAAGTTGTGGGCCTTAAGGA AACCAATAGCGGTTTCAGTGTCAACATCGTATTGGTGCTTG GTTGGTTCCATTGGCTTTGGTTCAATGAGG-3 |
| L | XI section 11 long reverse oligo | BBCHTS 2-17-05I OLIGO | 5-GCATACCAGCATCAACAGCACAGGCAAGTTCGTGTTCGA AAGTGTGACCAGCAAGAGTAGCGTGGTTAACTTCAATGTTG ACCTTGAAGTCCTTGTCTAAGTTGTGGGCC-3 |

TABLE 2-continued

The oligonucleotides A to R used in the gene assembly protocol adapted for the automated robotic platform.
OLIGONUCLEOTIDES USED IN THE PROMYCES XYLOSE ISOMERASE GENE ASSEMBLY STRATEGY

| OLIGO | DESCRIPTION | USDA NUMBER | SEQUENCE |
|---|---|---|---|
| M | XI section 12 long reverse oligo | BBCHTS 2-17-05J OLIGO | 5-GTTCGTATTGATCAATTGGGAATTGATCAGTATCCCAACCGTTTTGGTAGTCACCACGGTTAGCATCAATGGAACCGAGCATACCAGCATCAACAGCACAGGCAAGTTCG-3 |
| N | XI section 13 long reverse oligo | BBCHTS 2-17-05K OLIGO | 5-ACGACGAGTCTTGGCATCGAAGTTGGTACCACCAGTAACGAAACCACCACCACGGATGATTTCCATCCAAGCTTGGACGAGTTCGTATTGATCAATTGGGAATTGATCAG-3 |
| O | XI section 14 long reverse oligo | BBCHTS 2-17-05L OLIGO | 5-CTTGGCAGCGTTTTCAAGAGCACGAGCCATAGCATCCATACCAGAAACGTGGGCAATGATGATGTCTTCGAGGTCAGTAGAGTTACGACGAGTCTTGGCATCGAAGTTGG-3 |
| P | XI section 15 long reverse oligo | BBCHTS 2-17-05M OLIGO | 5-AAGTCCTTACCAATACCACTGTCGAAGGAAGCGTAACGTTCCTTCTTCATCTTGGTGTATGGAGATTCTTGGAGGAGCTTGGCAGCGTTTTCAAGAGCACGAGCCATAGC-3 |
| Q | XI section 16 long reverse oligo | BBCHTS 2-17-05N OLIGO | 5-TACCAGAAGTTTGCTTTGGTTCACCGTTCTTCTTACCGTATTCGTAAACTTGTTCGAGGGTGAGCTTACCATCTTCAAAGTCCTTACCAATACCACTGTCGAAGGAAGCG-3 |
| R | XI section 17 long reverse oligo | BBCHTS 2-17-05O OLIGO | 5-TTAACTACGATTAACTTATTGGTACATGGCAACAATGCTTCGTAGAGTTCTTGCTTACCAGAAGTTTGCTTTGGTTCACCGTTCTTCTTACCG-3 |

TABLE 3

Doubling times of strains grown aerobically in CM glucose or xylose URA/TRP/LEU selective liquid medium (control is XI-XKS).
Doubling Times

| strain | hours |
|---|---|
| Yeast Strain Doubling Time in 20% Glucose | |
| INVSc1-XI | 1.84 |
| INVSc1-XI-XKS | 1.84 |
| INVSc1-XI-Lyt-1 A6 | 1.86 |
| INVSc1-XI-Lyt-1 B9 | 1.92 |
| INVSc1-XI-Lyt-1 C3 | 1.91 |
| INVSc1-XI-Lyt-1 C6 | 1.90 |
| INVSc1-XI-Lyt-1 A6-XKS | 2.01 |
| INVSc1-XI-Lyt-1 B9-XKS | 1.98 |
| INVSc1-XI-Lyt-1 C3-XKS | 1.98 |
| INVSc1-XI-Lyt-1 C6-XKS | 1.96 |
| INVSc1-XI-Lyt-1 A6-TAL | 2.01 |
| INVSc1-XI-Lyt-1 B9-TAL | 2.02 |

TABLE 3-continued

Doubling times of strains grown aerobically in CM glucose or xylose URA/TRP/LEU selective liquid medium (control is XI-XKS).
Doubling Times

| strain | hours |
|---|---|
| INVSc1-XI-Lyt-1 C3-TAL | 1.96 |
| INVSc1-XI-Lyt-1 C6-TAL | 1.99 |
| Yeast Strain Doubling Time in 20% Xylose | |
| INVSc1-XI-XKS | 5.87 |
| INVSc1-XI-Lyt-1 A6-XKS | >20 |
| INVSc1-XI-Lyt-1 B9-XKS | >20 |
| INVSc1-XI-Lyt-1 C3-XKS | 18.40 |
| INVSc1-XI-Lyt-1 C6-XKS | 13.20 |
| INVSc1-XI-Lyt-1 A6-TAL | 0 |
| INVSc1-XI-Lyt-1 B9-TAL | 0 |
| INVSc1-XI-Lyt-1 C3-TAL | 0 |
| INVSc1-XI-Lyt-1 C6-TAL | 0 |

TABLE 4

Concentration of His-tagged protein in each band in FIG. 2C for XI and FIG. 4A for XI and Lyt-1 using AlphaEaseFC software for Windows 2000 to determine band density compared to known molecular weight markers from the Qiagen 6xHis-tagged set treated in the same fashion as the XI and Lyt-1 samples.

| | Analysis of HIS-Tagged Protein Concentration (ng/1 mL culture) | | | | |
|---|---|---|---|---|---|
| STRAIN | BAND ON GEL | AMOUNT TOTAL OF EACH HIS TAGGED BAND | SUM OF HIS XI PLUS HIS ENTK LYT-1 | SUM OF ALL HIS TAGGED | PERCENT INCREASE OVER ONE PLASMID EXPRESSION |
| INVSc1-XI (one plasmid) | HIS XI | 24477 | N/A | | |
| | HIS SUMO | 4771 | N/A | 29248 | 100 |
| INVSc1-XI-Lyt-1 C3 | HIS XI | 12101 | | | |
| (two plasmid) | HIS SUMO | 7845 | | | |
| | HIS ENTK LYT-1 | 18101 | 25506 | 33350 | 114 |
| INVSc1-XI-Lyt-1 A6 | HIS XI | 13101 | | | |
| | HIS SUMO | 7962 | | | |
| | HIS ENTK LYT-1 | 19943 | 27344 | 35326 | 121 |

TABLE 4-continued

Concentration of His-tagged protein in each band in FIG. 2C for XI and FIG. 4A for XI and Lyt-1 using AlphaEaseFC software for Windows 2000 to determine band density compared to known molecular weight markers from the Qiagen 6xHis-tagged set treated in the same fashion as the XI and Lyt-1 samples.

| | Analysis of HIS-Tagged Protein Concentration (ng/1 mL culture) | | | | |
|---|---|---|---|---|---|
| STRAIN | BAND ON GEL | AMOUNT TOTAL OF EACH HIS TAGGED BAND | SUM OF HIS XI PLUS HIS ENTK LYT-1 | SUM OF ALL HIS TAGGED | PERCENT INCREASE OVER ONE PLASMID EXPRESSION |
| INVSc1-XI-Lyt-1 B9 | HIS XI | 12229 | | | |
| | HIS SUMO | 8069 | | | |
| | HIS ENTK LYT-1 | 12786 | 25009 | 33092 | 113 |
| INVSc1-XI-Lyt-1 C6 | HIS XI | 13052 | | | |
| | HIS SUMO | 8047 | | | |
| | HIS ENTK LYT-1 | 11689 | 24721 | 33468 | 114 |
| INVSc1-XI-Lyt-1 C3-TAL (three plasmid) | HIS XI | 10475 | | | |
| | HIS SUMO | 18657 | | | |
| | HIS ENTK LYT-1 | 16026 | 26504 | 42861 | 147 |
| INVSc1-XI-Lyt-1 A6-TAL | HIS XI | 8106 | | | |
| | HIS SUMO | 16395 | | | |
| | HIS ENTK LYT-1 | 14133 | 23639 | 38734 | 132 |
| INVSc1-XI-Lyt-1 B9-TAL | HIS XI | 11752 | | | |
| | HIS SUMO | 13558 | | | |
| | HIS ENTK LYT-1 | 14757 | 26509 | 40064 | 137 |
| INVSc1-XI-Lyt-1 C6-TAL | HIS XI | 9676 | | | |
| | HIS SUMO | 15968 | | | |
| | HIS ENTK LYT-1 | 17106 | 26782 | 42768 | 146 |
| INVSc1-XI-Lyt-1 C3-XKS | HIS XI | 11894 | | | |
| | HIS SUMO | 12448 | | | |
| | HIS ENTK LYT-1 | 15075 | 26969 | 39415 | 135 |
| INVSc1-XI-Lyt-1 A6-XKS | HIS XI | 10097 | | | |
| | HIS SUMO | 14925 | | | |
| | HIS ENTK LYT-1 | 15877 | 25974 | 40900 | 140 |
| INVSc1-XI-Lyt-1 B9-XKS | HIS XI | 11124 | | | |
| | HIS SUMO | 13819 | | | |
| | HIS ENTK LYT-1 | 16969 | 30093 | 43712 | 149 |
| INVSc1-XI-Lyt-1 C6-XKS | HIS XI | 12188 | | | |
| | HIS SUMO | 13653 | | | |
| | HIS ENTK LYT-1 | 16955 | 29143 | 42696 | 146 |
| | KNOWN REFERENCE TO HIS TAGGED CONTROL MARKER AMOUNT | 250 | | | |

TABLE 5

Doubling times of *S. cerevisiae* double-plasmid and triple-plasmid diploid strains. Double-plasmid strains are derived from mating of PJ69-4 MATalpha strain expressing *Piromyces* XI with PJ69-4 MATa strain expressing one of the yeast library clones. Triple-plasmid strains are produced by transformation of double-plasmid strains with pSUMOduo RGStetHisXKS URA selectable plasmid. Cell concentration determined by optical density at 600 nm. Strains grown at 30° C. with 100 rpm shaking.
Doubling times in hours (using formula = LN(2)/((LN((time sq start/time sq stop))/10))
STRAIN DOUBLING TIME (hours; n = 3)

| GLUCOSE GROWTH On CM 2% glucose (-TRP-LEU medium) | | On CM 2% glucose (-TRP-LEU-URA medium) | |
|---|---|---|---|
| XI-PIP2* | 2.99 | XI-PIP2*-XKS | 3.91 |
| XI-IMG2 | 2.43 | XI-IMG2-XKS | 3.44 |
| XI-MAK5 | 5.87 | XI-MAK5-XKS | 5.39 |
| XI-VPS9 | 3.71 | XI-VPS9-XKS | 4.95 |
| XI-COX10 | 4.67 | XI-COX10-XKS | 4.11 |
| XI-ALE1 | 5.53 | XI-ALE1-XKS | 5.72 |
| XI-MMS4 | 4.20 | XI-MMS4-XKS | 3.89 |

| XYLOSE GROWTH On CM 2% xylose (-TRP-LEU medium) | On CM 2% xylose (-TRP-LEU-URA medium) |
|---|---|

TABLE 5-continued

Doubling times of *S. cerevisiae* double-plasmid and triple-plasmid diploid strains. Double-plasmid strains are derived from mating of PJ69-4 MATalpha strain expressing *Piromyces* XI with PJ69-4 MATa strain expressing one of the yeast library clones. Triple-plasmid strains are produced by transformation of double-plasmid strains with pSUMOduo RGStetHisXKS URA selectable plasmid. Cell concentration determined by optical density at 600 nm. Strains grown at 30° C. with 100 rpm shaking.
Doubling times in hours (using formula = LN(2)/((LN((time sq start/time sq stop))/10))
STRAIN DOUBLING TIME (hours; n = 3)

| | | | |
|---|---|---|---|
| XI-PIP2* | 8.33 | XI-PIP2*-XKS | 15.89 |
| XI-IMG2 | 5.43 | XI-IMG2-XKS | 11.79 |
| XI-MAK5 | 5.46 | XI-MAK5-XKS | 9.75 |
| XI-VPS9 | 7.67 | XI-VPS9-XKS | 17.02 |
| XI-COX10 | 12.46 | XI-COX10-XKS | 20.08 |
| XI-ALE1 | 11.90 | XI-ALE1-XKS | 17.44 |
| XI-MMS4 | 17.57 | XI-MMS4-XKS | 13.62 |

*Same as clone CDC7 so CDC7 was not analyzed.

TABLE 6

Sequence identification of seven unique clones that allow completely anaerobic growth on xylose and glucose. Saccharomyces Genome Database (SGD) nomenclature and function are given for the clones. Maximum ethanol productivity is given for *S. cerevisiae* diploid strains derived from mating of the PJ69-4 MATalpha bait strain expressing *Piromyces* XI attached to the binding domain (BD) of GAL4 with a PJ69-4 MATa strain expressing one of the yeast full-genome library clones attached to the GAL 4 activation domain (AD) and transformation with pSUMOduo RGStetHisXKS URA selectable plasmid. Measurements of ethanol were made after 100 hours at 30° C. with 100 rpm shaking.

Confirmation of Clone Identities and Maximum Ethanol from Alkaline Hydrolysate by Triple Plasmid Strains

| Strain with Constructs | NCBI GENE ID/ Gene name/Locus Tag/SGD ID | Clone Function | Maximum Ethanol* |
|---|---|---|---|
| PJ69-4 diploid-GAL4 BD XI background strain | not applicable | not applicable | 10.9 g/L |
| PJ69-4 diploid-GAL4 BD XI-RGStetHis XKS-GAL4 AD PIP2 | 854545/PIP2/YOR363C/S000005890 (same as YDL017W) | transcription factor | 14.0 g/L |
| PJ69-4 diploid-GAL4 BD XI-RGStetHis XKS-GAL4 AD IMG2 | 850434/IMG2/YCR071C/S000000667 | mitochondrial ribosomal protein of the small subunit | 14.3 g/L |
| PJ69-4 diploid-GAL4 BD XI-RGStetHis XKS-GAL4 AD MAK5 | 852439/MAK5/YBR142W/S000000346 | essential nucleolar protein | 13.9 g/L |
| PJ69-4 diploid-GAL4 BD XI-RGStetHis XKS-GAL4 AD VPS9 | 854876/VPS9/YML097C/S000004563 | vacuolar protein sorting | 13.8 g/L |
| PJ69-4 diploid-GAL4 BD XI-RGStetHis XKS-GAL4 AD COX10 | 855931/COX10/YPL172C/S000006093 | cytochrome c oxidase assembly protein, theme A: farnesyltransferase | 6.40 g/L |
| PJ69-4 diploid-GAL4 BD XI-RGStetHis XKS-GAL4 AD ALE1 | 854346/ALE1/YOR175C/S000005701 | lysophospholipid acyltransferase | 5.28 g/L |
| PJ69-4 diploid-GAL4 BD XI-RGStetHis XKS-GAL4 AD CDC7 | 851545/CDC7/YDL017W/S000002175 (same as YOR363C) | DDK (Dbf4-dependent kinase) catalytic subunit required for mitosis | (duplicate of PIP2) |
| PJ69-4 diploid-GAL4 BD XI-RGStetHis XKS-GAL4 AD MMS4 | 850915/MMS4/YLR218C/S000004208 | essential meiotic endonuclease | 14.1 g/L |

REFERENCES

Bang, S. S., and Pazirandeh, M., Physical properties and heavy metal uptake of encapsulated *Escherichia coli* expressing a metal binding gene (NCP). *J. Microencapsul.* 1999, 16(4):489-499

Blondelle et al. Influence of tryptophan residues on melittin's hemolytic activity. *Biochim. Biophys. Acta.* 1993, 1202 (2):331-336.

Butt et al. (2002) Methods and compositions for protein expression and purification. P02792US2 (KIT) U.S. patent application Ser. No. 10/504,785

Butt et al. (2002) Methods and compositions for protein expression and purification. International Patent Application No. PCT/US03/00436. U.S. Pat. No. 7,083,941 (issued Aug. 1, 2006)

Butt, T R.; Sterner, D and Zuo, X (2004) Compositions, methods and kits for enhancing protein expression, solubility and isolation. U.S. patent application Ser. No. 11/794,532

Butt et al. SUMO fusion technology for difficult-to-express proteins. Protein Expr. Purif. 2005, 43(1), 1-9.

Cagney et al. High-throughput screening for protein-protein interactions using the two-hybrid assay. *Meth. Enzynol.* 2000, 328, 3-14.

Christianson et al. Multifunctional yeast high-copy-number shuttle vectors. Gene 1992, 110(1):119-122.

Corzo et al. Oxyopinins, large amphipathic peptides isolated from the venom of the wolf spider *Oxyopes kitabensis* with cytolytic properties and positive insecticidal cooperativity with spider neurotoxins. *J. Biol. Chem.* 2002, 277(26): 23627-23637.

Den Haan et al. Functional expression of cellobiohydrolases in *Saccharomyces cerevisiae* towards one-step conversion of cellulose to ethanol. Enzym. Microb. Tech. 2007, 40:1291-1299.

Dien et al. Bacteria engineered for fuel ethanol production: current status. *App. Microbiol. Biotechnol.* 2003, 63(3):258-266.

Drees et al. A protein interaction map for cell polarity development. *J. Cell Biol.* 2001, 154(3):549-576.

Duguid et al. A physicochemical approach for predicting the effectiveness of peptide-based gene delivery systems for use in plasmid-based gene therapy. *Biophys. J.* 1998, 74(6): 2802-2814.

Farrell at al. Ethanol can contribute to energy and environmental goals. *Science* 2006, 311(5760):506-508.

Hahn-Hägerdal et al. Towards industrial pentose-fermenting yeast strains. *Appl. Microbiol. Biotechnol.* 2007, 74(5): 937-953.

Hamacher et al. Characterization of the xylose-transporting properties of yeast hexose transporters and their influence on xylose utilization. *Microbiology* 2002, 148:2783-2788.

Harhangi et al. Xylose metabolism in the anaerobic fungus *Piromyces* sp. E2 follows the bacterial pathway. *Arch. Microbiol.* 2003, 180:134-141.

Holm et al. Uptake of cell-penetrating peptides in yeasts. *FEBS Lett.* 2005, 579(23):5217-5222.

Hudson et al. The complete set of predicted genes from *Saccharomyces cerevisiae* in a readily usable form. *Genome Res.* 1997, 7(12):1169-1173.

Hughes et al. Automated Yeast Transformation Protocol to Engineer *Saccharomyces cerevisiae* Strains for Cellulosic Ethanol Production with Open Reading Frames That Express Proteins Binding to Xylose Isomerase Identified Using a Robotic Two-Hybrid Screen, *J. Assoc. Lab. Automat.* 2009, 14:200-212.

Hughes et al. Automated Yeast Mating Protocol Using Open Reading Frames from *Saccharomyces cerevisiae* Genome to Improve Yeast Strains for Cellulosic Ethanol Production, *J. Assoc. Lab. Automat.* 2009, 14:190-199.

Hughes et al. Lycotoxin-1 insecticidal peptide optimized by amino scanning mutagenesis and expressed as a coproduct in an ethanologenic *Saccharomyces cerevisiae* strain. *J. Pept. Sci.* 2008, published online in Wiley InterScience, DOI: 10.1002/psc.1040.

Hughes et al. Lycotoxin-1 insecticidal peptide optimized by amino scanning mutagenesis and expressed as a coproduct in an ethanologenic *Saccharomyces cerevisiae* strain. *J. Pept. Sci.* 2008, published online in Wiley InterScience, DOI: 10.1002/psc.1040.

Hughes et al. Cost-effective high-throughput fully automated construction of a multiplex library of mutagenized open reading frames for an insecticidal peptide using a plasmid-based functional proteomic robotic workcell with an improved vacuum system. *J. Assoc. Lab. Automat.* 2007, 12(4):202-212.

Hughes et al. Development of a liquid handler component for a plasmid-based functional proteomic robotic workcell. *J. Assoc. Lab. Autom.* 2005, 10(5):287-300.

Hughes et al. High-throughput screening of cellulase F mutants from multiplexed plasmid sets using an automated plate assay on a functional proteomic robotic workcell. *Proteome Science* 2006, 4:10.

Jeffries, T. W. Engineering yeasts for xylose metabolism. *Curr. Opin. Biotechnol.* 2006, 17(3):320-326.

Jeffries, T. W. and Jin, Y. S. Metabolic engineering for improved fermentation of pentoses by yeasts. *Appl. Microbiol. Biotechnol.* 2004, 63:495-509.

Jin et al. Optimal growth and ethanol production from xylose by recombinant *Saccharomyces cerevisiae* require moderate D-xylulokinase activity. *Appl. Environ. Microbiol.* 2003, 69(1):495-503.

Julian, G. R. and Jaynes, J. M., Methylated lysine-rich lytic peptides and method of making same by reductive alkylation. U.S. Pat. No. 5,717,064. Issued Feb. 10, 1998.

Karhumaa et al. Comparison of the xylose reductase-xylitol dehydrogenase and the xylose isomerase pathways for xylose fermentation by recombinant *Saccharomyces cerevisiae. Microb Cell Fact.* 2007, 6:5.

Karhumaa et al. Investigation of limiting metabolic steps in the utilization of xylose by recombinant *Saccharomyces cerevisiae* using metabolic engineering. *Yeast* 2005, 22:359-368.

Karpichev et al. Binding characteristics and regulatory mechanisms of the transcription factors controlling oleate-responsive genes in *Saccharomyces cerevisiae. J. Biol. Chem.* 2008, 283(16):10264-10275.

Karpichev, I. V. and Small, G. M. Global regulatory functions of Oaf1p and Pip2p (oaf2p), transcription factors that regulate genes encoding peroxisomal proteins in *Saccharomyces cerevisiae. Mol. Cell. Biol.* 1998, 18(11):6560-6570.

Kourie, J. I. and Shorthouse, A. A., Properties of cytotoxic peptide-formed ion channels. Am. J. Physiol. Cell Physiol. 2000, 278:C1063-C1087.

Kuyper et al. Evolutionary engineering of mixed-sugar utilization by a xylose-fermenting *Saccharomyces cerevisiae* strain. *FEMS Yeast Res.* 2005, 5:925-934.

Kuyper et al. High-level functional expression of a fungal xylose isomerase: the key to efficient ethanolic fermentation of xylose by *Saccharomyces cerevisiae? FS Yeast Res.* 2003 4(1):69-78.

Kuyper et al. Metabolic engineering of a xylose-isomerase-expressing *Saccharomyces cerevisiae* strain for rapid anaerobic xylose fermentation. *FEMS Yeast Res.* 2005, 5(4-5):399-409.

Kuyper et al. Minimal metabolic engineering of *Saccharomyces cerevisiae* for efficient anaerobic xylose fermentation: a proof of principle. *FEMS Yeast Res.* 2004 4(6): 655-664.

Li, S-J. and Hochstrasser, M., The Ulp1 SUMO isopeptidase: distinct domains required for viability, nuclear envelope localization, and substrate specificity. *J. Cell Biol.* 2003, 160 (7):1069-1081.

Locks, hon et al. The sensitivity of yeast mutants to oleic acid implicates the peroxisome and other processes in membrane function. Genetics 2007, 175(1):77-91.

Malakhov et al. SUMO fusions and SUMO-specific protease for efficient expression and purification of proteins. *J. Struc. Func. Genomics* 2004, 5(1-2):75-86.

Mayo et al. Structure-function relationships in novel peptide dodecamers with broad-spectrum bactericidal and endotoxin-neutralizing activities. *Biochem. J.* 2000 349:717-728.

Miller, G. L. Use of dinitrosalicylic acid reagent for determination of reducing sugar. *Anal. Chem.* 1959, 31:426-428.

Parenteau et al. Free uptake of cell-penetrating peptides by fission yeast. *FEBS Lett.* 2005, 579(21):4873-4878.

Peroutka R J, Elshourbagy N, Piech T, Butt T R (2008) Enhanced protein expression in mammalian cells using engineered SUMO fusions: secreted phospholipase A2. Protein Sci. 7:1586-95, Phizicky et al. Protein analysis on a proteomic scale. *Nature* 2003, 422:208-215.

Qureshi et al. Butanol production from wheat straw hydrolysate using *Clostridium beijerinckii. Bioprocess Biosyst Eng.* 2007, 30:419-427.

Rudolf et al. Simultaneous saccharification and fermentation of steam-pretreated bagasse using *Saccharomyces cerevisiae* TMB3400 and *Pichia stipitis* CBS6054. *Biotechnol. Bioeng.* 2007, 99(4):783-790.

Saha, B. C., Hemicellulose bioconversion. *J. Ind. Microbiol. Biotechnol.* 2003, 30(5):279-291.

Saha eat al. Dilute acid pretreatment, enzymatic saccharification, and fermentation of rice hulls to ethanol. *Biotechnol. Prog.* 2005, 21(3):816-822.

Saha, B. C. and Cotta, M. A. Ethanol production from alkaline peroxide pretreated enzymatically saccharified wheat straw. *Biotechnol. Prog.* 2006, 22:449-453.

Saha a al. Dilute acid pretreatment, enzymatic saccharification, and fermentation of rice hulls to ethanol. *Biotechnol. Prog.* 2005, 21:816-822.

Salzwedel et al. A conserved tryptophan-rich motif in the membrane-proximal region of the human immunodeficiency virus type 1 gp41 ectodomain is important for Env-mediated fusion and virus infectivity. *J. Virol.* 1999, 73(3):2469-24830

Sedlak, M. and Ho, N. W. Y., Production of ethanol from cellulosic biomass hydrolysates using genetically engineered *Saccharomyces* yeast capable of cofermenting glucose and xylose. *Appl, Biochem. Biotechnol.* 2004, 114(1-3):403-416.

Sheng, W. and Liao, X., Solution structure of a yeast ubiquitin-like protein Smt3: the role of structurally less defined sequences in protein-protein recognitions. Protein Science 2002, 11:1482-1491.

Stade et al. A lack of SUMO conjugation affects cNLS-dependent nuclear protein import in yeast. *J. Biol. Chem.* 2002, 277(51):49554-49561.

Sterner et al. Functional organization of the yeast SAGA complex: distinct components involved in structural integrity, nucleosome acetylation, and TATA-binding protein interaction. *Mol. Cell. Biol.* 1999, 19(1):86-98.

Toivola et al. Ethanoiic fermentation of D-xylose by yeasts. *Appl. Environ. Microbiol.* 1984, 47:1221-1223.

Uetz et al. A comprehensive analysis of protein-protein interactions in *Saccharomyces cerevisiae. Nature* 2000, 403: 623-627, Van Maris et al. Alcoholic fermentation of carbon sources in biomass hydrolysates by *Saccharomyces cerevisiae*: current status. *Antonie van Leeuwenhoek* 2006, 90(4):391-418.

Van Maris et al. Development of efficient xylose fermentation in *Saccharomyces cerevisiae*: xylose isomerase as a key component. *Adv. Biochem. Eng. Biotechnol.* 2007, 108:179-204.

Walfridsson et al. Ethanolic fermentation of xylose with *Saccharomyces cerevisiae* harboring the *Thermus thermophilus* xylA gene, which expresses an active xylose (glucose) isomerase. *Appl. Environ. Microbiol.* 1996, 62:4648-4651.

Wang, W. and Malcolm, B. A., Two-stage PCR protocol allowing introduction of multiple mutations, deletions and insertions using QuikChange Site-Directed Mutagenesis. *Biotechniques* 1999, 26(4):680-682.

Wisselink et al. Engineering of *Saccharomyces cerevisiae* for efficient anaerobic alcoholic fermentation of L-arabinose. Appl. Environ. Microbiol., 2007, 73(15):4881-4891.

Yan, L. and Adams, M. E., Lycotoxins, antimicrobial peptides from venom of the wolf spider *Lycosa carolinensis*. *J. Biol. Chem.* 1998, 273(4):2059-2066.

Zuo et al. PlasmID: a centralized repository for plasmid clone information and distribution. Nucleic Acids Res. 2007, 35 (Database issue):D680-D684.

We claim:

1. A recombinant xylose utilizing *Saccharomyces cerevisiae* yeast comprising heterologous polynucleotide sequences coding for xylulokinase and xylose isomerase, wherein said xylulokinase comprises *Yersinia pestis* xylulokinase.

2. The recombinant *Saccharomyces cerevisiae* yeast of claim 1 wherein said yeast expresses said heterologous polynucleotides at a sufficient functional level to grow aerobically on xylose as the sole carbon source.

3. The recombinant *Saccharomyces cerevisiae* yeast of claim 1 wherein said heterologous polynucleotides coding for xylulokinase and xylose isomerase are provided on one or more SUMO yeast expression vectors.

4. The recombinant *Saccharomyces cerevisiae* yeast of claim 1 wherein said heterologous polynucleotide sequences coding for xylulokinase and xylose isomerase are integrated into the chromosome of said yeast.

5. The recombinant *Saccharomyces cerevisiae* yeast of claim 1 wherein said yeast grows aerobically on xylose as the sole carbon source at a greater rate than the parent *Saccharomyces cerevisiae* yeast from which it was derived.

6. The recombinant *Saccharomyces cerevisiae* yeast of claim 5 comprising a doubling time of less than approximately 12 hours when cultured aerobically on CM 2% xylose liquid medium at 30° C.

7. The recombinant *Saccharomyces cerevisiae* yeast of claim 5 comprising a doubling time of less than approximately 6 hours when cultured aerobically on CM 2% xylose liquid medium at 30° C.

8. The recombinant *Saccharomyces cerevisiae* yeast of claim 1 wherein said yeast is deposited as accession no. NRRL Y-50183.

9. The recombinant *Saccharomyces cerevisiae* yeast of claim 1 wherein said xylose isomerase comprises *Piromyces* sp. E2 xylose isomerase.

10. The recombinant *Saccharomyces cerevisiae* yeast of claim 1 further transformed with one or more genes selected from the group consisting of cellulases, hemicellulases, peroxidases, laccases, chitinases, proteases, and pectinases.

11. The recombinant *Saccharomyces cerevisiae* yeast of claim 1 further transformed with one or more native *Saccharomyces cerevisiae* polynucleotide sequences selected from the group consisting of PIP2, IMG2, MAK5, VPS9, COX10, ALE1, CDC7, and MMS4, and over-expressing said native polynucleotide sequences at a sufficient level that said yeast is capable of anaerobic growth on xylose as the sole carbon source.

12. The recombinant *Saccharomyces cerevisiae* yeast of claim 11 further transformed with the native *Saccharomyces cerevisiae* polynucleotide sequences for ADH1 and COX10.

13. The recombinant *Saccharomyces cerevisiae* yeast of claim 12 wherein said yeast is *Saccharomyces cerevisiae* XI-XKS-COX10-ADH1::PJ69-4, deposited as accession no. NRRL Y-50328.

14. The recombinant *Saccharomyces cerevisiae* yeast of claim 11 wherein said yeast grows anaerobically on xylose as the sole carbon source at a greater rate than the parent *Saccharomyces cerevisiae* yeast from which it was derived which is not transformed with said native polynucleotide sequences.

15. The recombinant *Saccharomyces cerevisiae* yeast of claim 14 comprising a doubling time of less than approximately 24 hours when cultured anaerobically on CM 2% xylose liquid medium at 30° C.

16. The recombinant *Saccharomyces cerevisiae* yeast of claim 11 wherein said yeast expresses said heterologous polynucleotide sequences at a sufficient functional level so as to facilitate the fermentation of glucose to ethanol.

17. The recombinant *Saccharomyces cerevisiae* yeast of claim 11 wherein said one or more genes are selected from the group consisting of PIP2, IMG2, and MMS4.

18. The recombinant *Saccharomyces cerevisiae* yeast of claim 11 further transformed with one or more genes selected from the group consisting of cellulases, hemicellulases, peroxidases, laccases, chitinases, proteases, and pectinases.

19. A method of producing ethanol comprising growing the recombinant *Saccharomyces cerevisiae* yeast of claim 11 on a culture medium comprising glucose and xylose under anaerobic conditions for a period of time effective to allow said yeast to grow on said xylose and ferment said glucose to ethanol.

20. The method of claim 19 wherein said culture medium comprises a hydrolysate of a lignocellulosic material.

* * * * *